US012728118B2

(12) United States Patent
Jurkunas

(10) Patent No.: US 12,728,118 B2
(45) Date of Patent: Sep. 8, 2026

(54) METHODS AND COMPOSITIONS FOR THE TREATMENT OF CORNEAL ENDOTHELIUM DISORDERS

(71) Applicant: The Schepens Eye Research Institute, Inc., Boston, MA (US)

(72) Inventor: Ula Jurkunas, Winchester, MA (US)

(73) Assignee: The Schepens Eye Research Institute, Inc., Boston, MA (US)

(*) Notice: Subject to any disclaimer, the term of this patent is extended or adjusted under 35 U.S.C. 154(b) by 422 days.

(21) Appl. No.: 18/267,905

(22) PCT Filed: Dec. 22, 2021

(86) PCT No.: PCT/US2021/064877
§ 371 (c)(1),
(2) Date: Jun. 16, 2023

(87) PCT Pub. No.: WO2022/140551
PCT Pub. Date: Jun. 30, 2022

(65) Prior Publication Data

US 2024/0108608 A1 Apr. 4, 2024

Related U.S. Application Data

(60) Provisional application No. 63/130,246, filed on Dec. 23, 2020.

(51) Int. Cl.

| | |
|---|---|
| ***A61K 31/4375*** | (2006.01) |
| ***A61K 9/00*** | (2006.01) |

(Continued)

(52) U.S. Cl.
CPC ........ *A61K 31/4375* (2013.01); *A61K 9/0048* (2013.01); *A61K 31/09* (2013.01);
(Continued)

(58) Field of Classification Search
CPC .. A61K 31/4375; A61K 9/0048; A61K 31/09; A61K 31/352; A61K 45/00; A61K 31/136; A61K 31/138; A61K 31/167; A61K 31/337; A61K 31/704; A61K 31/7105; A61P 27/02; A61P 27/06; A61P 27/12; A61P 29/00
(Continued)

(56) References Cited

U.S. PATENT DOCUMENTS

| | | | |
|---|---|---|---|
| 4,522,811 | A | 6/1985 | Eppstein et al. |
| 6,127,128 | A | 10/2000 | Sarfarazi et al. |

(Continued)

FOREIGN PATENT DOCUMENTS

| | | |
|---|---|---|
| CN | 101375848 | 3/2009 |
| CN | 105997872 | 10/2016 |

(Continued)

OTHER PUBLICATIONS

Extended European Search Report in European Appln. No. 21912145.6, dated Oct. 8, 2024, 8 pages.

(Continued)

*Primary Examiner* — Taylor V Oh
(74) *Attorney, Agent, or Firm* — Fish & Richardson P.C.

(57) ABSTRACT

This application discloses methods and pharmaceutical compositions (e.g., oral, parenteral or topical ophthalmic formulations) for treating Fuchs endothelial corneal dystrophy (FECD).

6 Claims, 24 Drawing Sheets

(51) Int. Cl.

| | |
|---|---|
| ***A61K 31/09*** | (2006.01) |
| ***A61K 31/352*** | (2006.01) |
| ***A61K 45/00*** | (2006.01) |
| ***A61P 27/02*** | (2006.01) |

(52) U.S. Cl.
CPC ........... *A61K 31/352* (2013.01); *A61K 45/00* (2013.01); *A61P 27/02* (2018.01)

(58) Field of Classification Search
USPC .......................................................... 514/280
See application file for complete search history.

(56) References Cited

U.S. PATENT DOCUMENTS

| | | | |
|---|---|---|---|
| 6,468,798 | B1 | 10/2002 | Debs et al. |
| 2007/0026034 | A1 | 2/2007 | Burke et al. |
| 2016/0339008 | A1 | 11/2016 | Smith et al. |
| 2020/0255859 | A1 | 8/2020 | Yang et al. |

FOREIGN PATENT DOCUMENTS

| | | |
|---|---|---|
| CN | 111991391 | 11/2020 |
| WO | WO 2022/257986 | 12/2022 |

OTHER PUBLICATIONS

Shetty et al., "Elevated expression of matrix metalloproteinase-9 and inflammatory cytokines in keratoconus patients is inhibited by cyclosporine A," Invest Ophthalmol Vis Sci., Feb. 2015, 56(2):738-50.

Adamis et al., "Fuchs' endothelial dystrophy of the cornea," Surv. Ophthalmol., Sep.-Oct. 1993, 38(2):149-168.

Afshari et al., "Genome-wide association study identifies three novel loci in Fuchs endothelial corneal dystrophy," Nat. Commun., Mar. 2017, 8:14898, 8 pages.

Badal and Delgoda, "CYP1B1: friend or foe? A critical review," OA Biochemistry, Apr. 2013, 1(1):8, 7 pages.

Bansal et al., "Mitochondrial Targeting of Cytochrome P450 (Cyp) 1B1 and Its Role in Polycyclic Aromatic Hydrocarbon-induced Mitochondrial Dysfunction," J. Biol. Chem., Apr. 2014, 289(14):9936-9951.

Baratz et al., "E2-2 protein and Fuchs's corneal dystrophy," N. Engl. J. Med., Sep. 2010, 363(11):1016-1024.

Behrendt et al., "Induction of cytochrome P450 1 genes and stress response genes in developing zebrafish exposed to ultraviolet radiation," Aquat. Toxicol., Jun. 2010, 98(1):74-82.

Benischke et al., "Activation of mitophagy leads to decline in Mfn2 and loss of mitochondrial mass in Fuchs endothelial corneal dystrophy," Sci. Rep., Jul. 2017, 7(1):6656, 11 pages.

Bergmanson, "Corneal damage in photokeratitis—Why is it so painful?," Optom. Vis. Sci., Jun. 1990, 67(6):407-413.

Biswas et al., "Missense mutations in COL8A2, the gene encoding the alpha2 chain of type VIII collagen, cause two forms of corneal endothelial dystrophy," Hum. Mol. Genet., Oct. 2001, 10(21):2415-2423.

Bourges et al., "Intraocular implants for extended drug delivery: therapeutic applications," Adv Drug Deliv Rev, Nov. 2006, 58(11):1182-1202.

Bourges et al., "Ocular drug delivery targeting the retina and retinal pigment epithelium using polylactide nanoparticles," Invest Opth Vis Sci, Aug. 2003, 44:3562-9.

Buters et al., "Cytochrome P450 CYP1B1 determines susceptibility to 7,12- dimethylbenz[β]anthracene-induced lymphomas," Proc. Natl. Acad. Sci. U.S.A., Mar. 1999, 96(5):1977-1982.

Byers et al., "Mouse estrous cycle identification tool and images," PLoS One, 2012, 7(4):e35538, 5 pages.

CAS No. 24144-92-1, "2,4,3',5'-tetramethoxystilbene," Sigma-Aldrich, retrieved on Apr. 18, 2024, retrieved from URL <https://www.sigmaaldrich.com/US/en/product/sigma/smb00388>, 7 pages.

Cavalieri and Rogan, "Unbalanced metabolism of endogenous estrogens in the etiology and prevention of human cancer," J. Steroid Biochem. Mol. Biol., Jul. 2011, 125(3-5):169-180.

Cavalieri et al., "Catechol estrogen quinones as initiators of breast and other human cancers: Implications for biomarkers of susceptibility and cancer prevention," Biochim. Biophys. Acta., Aug. 2006, 1766(1):63-78.

Cavalieri et al., "Critical depurinating DNA adducts: Estrogen adducts in the etiology and prevention of cancer and dopamine adducts in the etiology and prevention of Parkinson's disease," Int. J. Cancer, Sep. 2017, 141(6):1078-1090.

Cavalieri et al., "Molecular origin of cancer: Catechol estrogen-3,4-quinones as endogenous tumor initiators," Proc. Natl. Acad. Sci. U.S.A., Sep. 1997, 94(20):10937-10942.

Chang et al., "Cytochrome P450 1B1 inhibition suppresses tumorigenicity of prostate cancer via caspase-1 activation," Oncotarget, Jun. 2017, 8(24):39087-39100.

Chung et al., "Functional impact of ZEB1 mutations associated with posterior polymorphous and Fuchs' endothelial corneal dystrophies," Invest. Ophthalmol. Vis. Sci., Oct. 2014, 55:6159-6166.

Cullen, "Photokeratitis and other phototoxic effects on the cornea and conjunctiva," Int. J. Toxicol., Nov.-Dec. 2002, 21(6):455-464.

Doutch et al., "Ultraviolet light transmission through the human corneal stroma is reduced in the periphery, " Biophys. J., Mar. 2012, 102(6):1258-1264.

Gaikwad et al., "Imbalanced estrogen metabolism in the brain: Possible relevance to the etiology of Parkinson's disease," Biomarkers, Aug. 2011, 16(5):434-444.

Ghate et al., "Ocular drug delivery," Expert Opin Drug Deliv, Feb. 2006, 3(2):275-87.

Goerz et al., "Influence of UVA and UVB irradiation on hepatic and cutaneous P450 isoenzymes," Arch. Dermatol. Res., Dec. 1996, 289(1):46-51.

Gottsch et al., "Inheritance of a novel COL8A2 mutation defines a distinct earlyonset subtype of fuchs corneal dystrophy," Invest. Ophthalmol. Vis. Sci., Jun. 2005, 46(6):1934-1939.

Gottsch et al., "Serial analysis of gene expression in the corneal endothelium of Fuchs' dystrophy," Invest. Ophthalmol. Vis. Sci., Feb. 2003, 44(2):594-599.

Hakkola et al., "Expression of CYP1B1 in human adult and fetal tissues and differential inducibility of CYP1B1 and CYP1A1 by Ah receptor ligands in human placenta and cultured cells," Carcinogenesis, Feb. 1997, 18(2):391-397.

Halilovic et al., "Menadione-induced DNA damage leads to mitochondrial dysfunction and fragmentation during rosette formation in Fuchs endothelial corneal dystrophy," Antioxid. Redox Signal., Jun. 2016, 24(18):1072-1083.

Hogan et al., "Fuchs' endothelial dystrophy of the cornea. 29th Sanford Gifford Memorial lecture," Am. J. Ophthalmol., Sep. 1974, 78(3):363-383.

Horley et al., "Discovery and characterization of novel CYP1B1 inhibitors based on heterocyclic chalcones: Overcoming cisplatin resistance in CYP1B1-overexpressing lines," European Journal of Medicinal Chemistry, Mar. 2017, 129:159-174.

International Preliminary Report on Patentability in International Appln. No. PCT/US2021/064877, mailed Jul. 6, 2023, 7 pages.

International Search Report & Written Opinion in International Appln. No. PCT/US2021/064877, mailed Mar. 18, 2022, 9 pages.

Joyce et al., "Age-related gene response of human corneal endothelium to oxidative stress and DNA damage," Invest. Ophthalmol. Vis. Sci., Mar. 2011, 52(3):1641-1649.

Joyce et al., "Relationship among oxidative stress, DNA damage, and proliferative capacity in human corneal endothelium," Invest. Ophthalmol. Vis. Sci., May 2009, 50(5):2116-2122.

Joyce, "Proliferative capacity of the corneal endothelium," Prog. Retin. Eye Res., May 2003, 22(3):359-389.

Jun et al., "An alpha 2 collagen VIII transgenic knock-in mouse model of Fuchs endothelial corneal dystrophy shows early endothelial cell unfolded protein response and apoptosis," Hum. Mol. Genet., Jan. 2012, 21(2):384-393.

Jurkunas et al., "Decreased expression of peroxiredoxins in Fuchs' endothelial dystrophy," Invest. Ophthalmol. Vis. Sci., Jul. 2008, 49(7):2956-2963.

(56) References Cited

OTHER PUBLICATIONS

Jurkunas et al., "Evidence of oxidative stress in the pathogenesis of fuchs endothelial corneal dystrophy," Am. J. Pathol., Nov. 2010, 177(5):2278-2289.
Jurkunas, "Fuchs endothelial corneal dystrophy through the prism of oxidative stress," Cornea, Nov. 2018, 37(Suppl. 1):S50-S54.
Liu et al., "Ultraviolet A light induces DNA damage and estrogen DNA adducts in Fuchs endothelial corneal dystrophy causing females to be more affected," PNAS, Dec. 2019, 117(1):573-583.
Liu et al., "UV-A irradiation activates Nrf2-regulated antioxidant defense and induces p53/caspase3-dependent apoptosis in corneal endothelial cells," Invest. Ophthalmol. Vis. Sci., Apr. 2016, 57(4):2319-2327.
Matthaei et al., "Fuchs endothelial corneal dystrophy: Clinical, genetic, pathophysiologic, and therapeutic aspects," Annu. Rev. Vis. Sci., Sep. 2019, 5:151-175.
Meng et al., "L450W and Q455K Col8a2 knock-in mouse models of Fuchs endothelial corneal dystrophy show distinct phenotypes and evidence for altered autophagy," Invest. Ophthalmol. Vis. Sci., Mar. 2013, 54(3):1887-1897.
Miyai et al., "Activation of PINK1-Parkin-Mediated Mitophagy Degrades Mitochondrial Quality Control Proteins in Fuchs Endothelial Corneal Dystrophy," Am. J. Pathol., Oct. 2019, 189(10):2061-2076.
Mondal et al., "Modulation of cellular response to arsenic trioxide toxicity by resveratrol," ACS Omega, May 2018, 3(5):5511-5515.
Nadler et al., "Abstract 2544: Anti-CYP1B1 biologic and clinical responses are induced in patients with advanced stage solid tumors with cyclophosphamide pre-dosing and immunization with ZYC300," Abstract, Presented at Proceedings of the 99th AACR Annual Meeting, San Diego, CA, Apr. 12-16, 2008; Cancer Res, May 2008, 68(9_Supplement): 2544, 2 pages.
Pelkonen et al., "Tissue and sex-dependent differences in CYP2A activities in hamsters," Arch. Toxicol., Jul. 1994, 68:416-422.
Pruthi et al., "Evaluation of serum estrogen-DNA adducts as potential biomarkers for breast cancer risk," HHS Public Access Author Manuscript, doi: 10.1016/j.jsbmb.2012.02.002, published online Oct. 1, 2013; published in final edited form as: J. Steroid Biochem. Mol. Biol., Oct. 2012, 132(1-2):73-79, 19 pages.
Riazuddin et al., "Mutations in LOXHD1, a recessive-deafness locus, cause dominant late-onset Fuchs corneal dystrophy," Am. J. Hum. Genet., Mar. 2012, 90:533-539.
Ridley et al., "Cellular and subcellular responses to UVA in relation to carcinogenesis," Int. J. Radiat. Biol., Jul. 2009, 85(3):177-195.
Rochat et al., "Human CYP1B1 and Anticancer Agent Metabolism: Mechanism for Tumor-Specific Drug Inactivation?," Journal of Pharmacology and Experimental Therapeutics, Feb. 2001, 296(2):537-541.
Sangar et al., "Bimodal targeting of microsomal cytochrome P450s to mitochondria: Implications in drug metabolism and toxicity," HHS Public Access Author Manuscript, doi: 10.1517/17425255.2010.503955, published online Oct. 1, 2011; published in final edited form as: Expert Opin. Drug Metab. Toxicol., Oct. 2010, 6(10):1231-1251, 32 pages.
Santos et al., "Measuring oxidative mtDNA damage and repair using quantitative PCR," Methods Mol. Biol., 2002, 197:159-176.
Schmedt et al., "Molecular bases of corneal endothelial dystrophies," HHS Public Access Author Manuscript, doi: 10.1016/j.exer.2011.08.002, published online Feb. 1, 2013; published in final edited form as: Exp. Eye Res., Feb. 2012, 95(1):24-34, 23 pages.
Schmedt et al., "Telomerase immortalization of human corneal endothelial cells yields functional hexagonal monolayers," PLoS One, 2012, 7(12):e51427, 11 pages.
Sharma et al., "Intrinsic mitochondrial DNA repair defects in Ataxia Telangiectasia," DNA Repair (Arnst.), Jan. 2014, 13:22-31.
Short, "Safety Evaluation of Ocular Drug Delivery Formulations: Techniques and Practical Considerations," Toxicol Pathol, Jan. 2008, 36(1):49-62.
Sindhu et al., "Induction of cytochrome p450 1A1 and 1B1 by photooxidized tryptophan in transformed human keratinocytes," Adv. Exp. Med. Biol., 2003, 527:297-306.
Smolin and Thoft's The Cornea: Scientific Foundations and Clinical Practice, 4th Ed., Foster et al. (eds)., 2004, Chapter 47, 26 pages.
Sun, "N-acetylcysteine, reactive oxygen species and beyond," Cancer Biol. Ther., Jan. 2010, 9(2):109-110.
Thomas and Roy, "Base sequence-specific attack of stilbene estrogen metabolite(s) on the mitochondrial DNA: Implications in the induction of instability in the mitochondrial genome in the kidney of Syrian hamsters," Int. J. Mol. Med., Apr. 2001, 7(4):389-395.
Thomas and Roy, "Stilbene estrogen produces higher levels of mitochondrial DNA adducts than nuclear DNA adducts in the target organ of cancer (liver) of male Sprague Dawley rats," Oncol. Rep., Sep.-Oct. 2001, 8(5):1035-1038.
Vasiliou and Gonzalez, "Role of CYP1B1 in glaucoma," Annu. Rev. Pharmacol. Toxicol., 2008, 48:333-358.
Vile and Tyrrell, "UVA radiation-induced oxidative damage to lipids and proteins in vitro and in human skin fibroblasts is dependent on iron and singlet oxygen," Free Radic. Biol. Med., Apr. 1995, 18(4):721-730.
Wieben et al., "A common trinucleotide repeat expansion within the transcription factor 4 (TCF4, E2-2) gene predicts Fuchs corneal dystrophy," PLoS One, Nov. 2012, 7(11):e49083, 8 pages.
Wilson and Bourne, "Fuchs' dystrophy," Cornea, 1988, 7(1):2-18.
Wollensak et al., "Corneal endothelial cytotoxicity of riboflavin/UVA treatment in vitro," Ophthalmic Res., Nov.-Dec. 2003, 35(6):324-328.
Wollensak et al., "Endothelial cell damage after riboflavinultraviolet—A treatment in the rabbit," J. Cataract Refract. Surg., Sep. 2003, 29(9):1786-1790.
Yakes and Van Houten, "Mitochondrial DNA damage is more extensive and persists longer than nuclear DNA damage in human cells following oxidative stress," Proc. Natl. Acad. Sci. U.S.A., Jan. 1997, 94(2):514-519.
Young, "Acute effects of UVR on human eyes and skin," Prog. Biophys. Mol. Biol., Sep. 2006, 92(1):80-85.
Zahid et al., "Unbalanced estrogen metabolism in ovarian cancer," Int. J. Cancer, May 2014, 134(10):2414-2423.
Zhang et al., "Fuchs' Genetics Multi-Center Study Group, Association of smoking and other risk factors with Fuchs' endothelial corneal dystrophy severity and corneal thickness," Invest. Ophthalmol. Vis. Sci., Aug. 2013, 54:5829-5835.
Zhang et al., "The molecular basis of fuchs' endothelial corneal dystrophy, " Mol. Diagn. Ther., Feb. 2019, 23(1):97-112.
Zinflou and Rochette, "Ultraviolet A-induced oxidation in cornea: Characterization of the early oxidation-related events," Free Radie. Biol. Med., Jul. 2017, 108:118-128.
Zoega et al., "Prevalence and risk factors for cornea guttata in the Reykjavik Eye Study," Ophthalmology, Apr. 2006, 113(4):565-569.
Feizi et al., "Corneal endothelial cell dysfunction: etiologies and management," Therapeutic Advances in Ophthalmology, Dec. 2018, 10:2515841418815802, 19 pages.
Office Action in European Appln. No. 21912145.6, mailed on Dec. 8, 2025, 6 pages.

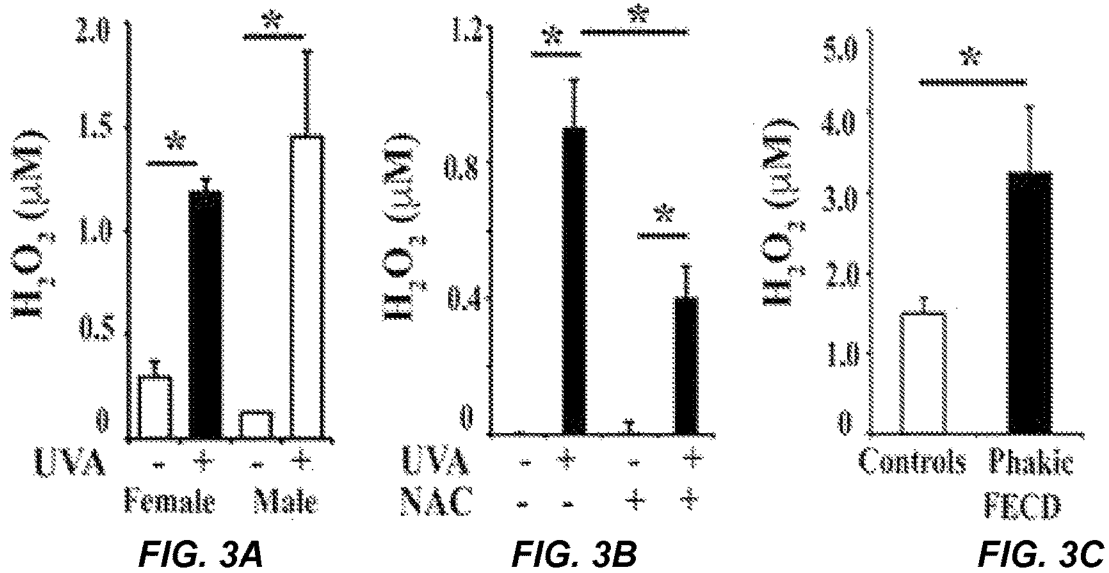
FIG. 3A
FIG. 3B
FIG. 3C
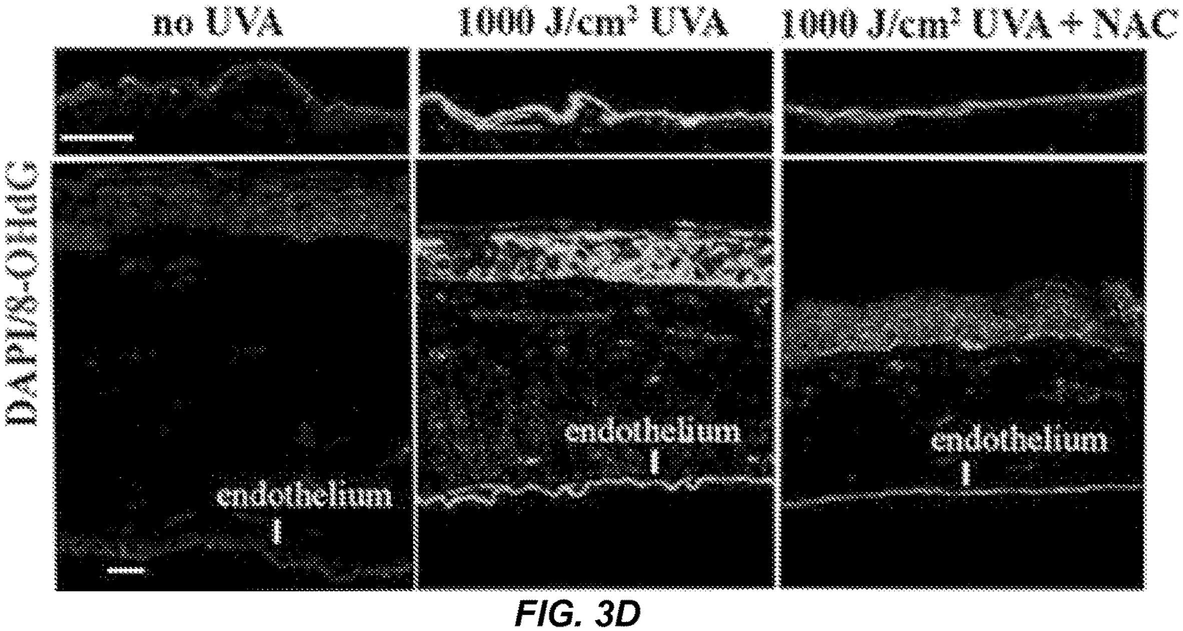
FIG. 3D

METHODS AND COMPOSITIONS FOR THE TREATMENT OF CORNEAL ENDOTHELIUM DISORDERS

CLAIM OF PRIORITY

This application is the national stage entry of International Patent Application No. PCT/US2021/064877, filed on Dec. 22, 2021, and claims the benefit of U.S. Provisional Patent Application Ser. No. 63/130,246, filed on Dec. 23, 2020. The entire contents of the foregoing are hereby incorporated by reference.

FEDERALLY SPONSORED RESEARCH OR DEVELOPMENT

This invention was made with Government support under Grant Nos. EY020581 and EY003790 awarded by the National Institutes of Health/National Eye Institute. The Government has certain rights in the invention.

TECHNICAL FIELD

The present invention relates to compositions and methods for the treatment of corneal endothelium disorders.

BACKGROUND

Fuchs endothelial corneal dystrophy (FECD) is a progressive, blinding disease characterized by corneal endothelial (CE) cell apoptosis. It is an age-related complex disorder resulting from the multifactorial interplay of genetic mutations and environment. The disease, predominant in females (3:1), manifests in the progressive degeneration of post-mitotically arrested corneal endothelial monolayer of cells, derived from the neural crest. In FECD, progressive loss of the endothelial cell density leads to corneal edema, scarring, and loss of vision.

FECD affects approximately 1% of general population, while corneal guttae can be detected in about 4-6% of general population. FECD is the second most common cause for corneal transplants done in the U.S. in >50 year-old age group.

Even though this dystrophy has been described in early 1900's, there is no known treatment for this disorder, and the only modality that restores lost vision is corneal transplantation. Development of pharmacotherapeutics that could prevent endothelial cell loss in early, as well as late stages of the disease would address one of most pressing unmet medical needs in ophthalmology.

SUMMARY

Provided herein are methods for inhibiting or treating a disease or pathology of the Cornea in a subject, the method comprising administering to the subject a therapeutically effective dose of cytochrome P450 enzyme inhibitor.

In one embodiment, the disease or pathology of the cornea is a corneal endothelial cell disorder.

In one embodiment, the disease or pathology of the cornea is Fuchs endothelial corneal dystrophy (FECD) or corneal ectasia.

In one embodiment, the corneal ectasia is keratoconus.

In one embodiment, the subject has had previous cataract surgery.

In one embodiment, the cytochrome P450 enzyme is not CYP1B1.

In one embodiment, the cytochrome P450 enzyme is CYP1B1, CYP1A1, CYP1A2, CYP2A6, CYP2C8, CYP2C19, CYP2D6, CYP3A4, CYP2C9, or CYP4F2.

In one embodiment, wherein the cytochrome P450 enzyme is CYP1B1.

In one embodiment, the cytochrome P450 enzyme inhibitor is a small molecule, a shRNA, a microRNA, an antisense oligonucleotide or an antibody.

In one embodiment, the small molecule inhibitor is: (a) a Chromene amide; (b) a prenylated bromo hydroquinone; (c) a flavone; (d) a pyridylchalcone; (e) a flavanone; (f) a flavonole; (g) a stilbene or variant thereof; (h) an Anthraquinone pigment; (i) flutamide; (j) paclitaxel; (k) mitoxantrone; (l) docetaxel; (m) doxorubicin; (n) daunomycin; or (o) tamoxifen.

In one embodiment, the stilbene is trans-2,3',4,5'-tetramethoxystilbene.

In one embodiment, the cytochrome P450 enzyme inhibitor is luteolin, apigenin, Kaempferol, or berberine.

In one embodiment, the cytochrome P450 enzyme inhibitor is not quercetin.

In one embodiment, administration is made locally to the eye.

In one embodiment, local administration to the eye is by topical administration or by eye drops.

In some embodiments, the subject is human, e.g. a female.

Also provided herein are pharmaceutical ophthalmic compositions comprising a therapeutically effective dose of cytochrome P450 enzyme inhibitor and an ophthalmically-compatible excipient.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

(FIG. 1A) Slit lamp images of FECD patient corneas are shown in the Left (broadbeam) and Middle (retroillumination) panels. White arrows indicate guttae, the dashed circle indicates the central cornea, and the white dashed line denotes the eyelid boundary. (Right) A corresponding HRT image of the patient cornea. Arrowheads indicate guttae. (FIG. 1B) In vivo confocal HRT photographs of female and male MCEnCs with 500, 1,000 J/cm$^2$ UVA or 1,000 J/cm$^2$ UVA with NAC treatment at time points corresponding to 1 d, 2 wk, and 1, 2, and 3 mo post-UVA. (Scale bar, 100 μm) (FIG. 1C) Cell density analysis of female (top), male (middle), and NAC-treated mice (bottom) up to 2 mo post-UVA. n=4 for 250, 500, or 750 J/cm$^2$ male or female treatments; n=13 for male-1,000 J/cm$^2$ treatments; n=12 for 1,000 J/cm$^2$ treatments in female mouse corneas; n=8 for male-1,000 J/cm$^2$ with NAC treatment; n=7 for female-1,000 J/cm$^2$ with NAC treatment. (Left and Middle) The * indicates the significant difference between UVA doses; the + denotes the significant difference between NAC- and non-NAC treatment ($P<0.05$). (Right) The * indicates significant difference between the males and females or NAC and non-NAC treatment ($P<0.05$).

(FIG. 2A, Upper) Representative confocal images of whole mount of mouse MCEnCs detecting ZO-1 localization at 3 mo post-UVA. Shown are ZO-1 immunostaining-based analysis for hexagonality (Lower Left), coefficient of variation (Lower Middle), and cell density (Lower Right) for MCEnCs from females and males at 3 mo post-UVA (n=3). Data are mean±SEM. (Scale bar, 50 μm) (FIG. 2B) Representative OCT images of mouse corneas at 1 mo post-UVA (female, Upper; male, Lower). (FIG. 2C) OCT image-based CCT analysis. Mixed-effect regression analysis was employed to analyze the effect of 250, 500, 750, and 1,000 $J/cm^2$ UVA, and 1,000 $J/cm^2$ UVA with NAC treatment on CCT changes. n=4 for 250, 500, and 750 $J/cm^2$ UVA treatments; n=21 and n=18 for male and female 1,000 $J/cm^2$ treatment; n=8 and n=6 for NAC-treatment of male and females irradiated with 1,000 $J/cm^2$ UVA. Data are mean±SEM; $P<0.05$. The * represents the difference between non-NAC males and non-NAC females; the + represents the difference between post-UVA and pre-UVA for non-NAC females; the #represents the difference between post-UVA and pre-UVA for non-NAC males. The a and b indicate the difference in HRT between non-NAC and NAC-treated females and males 3 mo after 1,000 $J/cm^2$ UVA, respectively.

FIGS. 3A-3N. UVA irradiation induced ROS, DNA damage, mitochondria swelling, and cell apoptosis in MCEnCs. (FIG. 3A) $H_2O_2$-based ROS production in the aqueous humor from 1,000 $J/cm^2$ UVA-treated eyes immediately post-UVA (n=3) and control eyes. (FIG. 3B) ROS production in the aqueous humor from mice with or without NAC treatment 1 d post-UVA (n=4). (FIG. 3C) $H_2O_2$-based ROS production in the aqueous humor from phakic FECD (with native lens) patients (n=7) and controls (cataract patients, n=16). *$P<0.05$, Student's t test. (FIG. 3D) Representative confocal images of whole mount of the mouse CE with 8-OHdG labeling 3 mo after 1,000 $J/cm^2$ UVA. DAPI was used for nuclei staining. (Scale bars, 50 μM) (FIG. 3E and FIG. 3F) Representative confocal images of whole mount of the female (Upper) and male (Lower) mouse CE with TUNEL labeling 3 mo after 500 $J/cm^2$ or 1,000 $J/cm^2$ UVA and the corresponding quantification of percent TUNEL-positive cells. DAPI was used for nuclei staining. White asterisks indicate rosette formation. (Scale bar, 50 μm) *$P<0.05$, Student's t test. Detection of MCEnC mtDNA (FIG. 3G), nDNA (FIG. 3H and FIG. 3I) damage, and DNA lesions using LA-qPCR analysis. The horizontal dotted lines in FIGS. 3G-3I indicate the normalization of the corresponding untreated OS eye for each time point to 1. Data are mean±SEM, *$P<0.05$ by 2-way ANOVA. (FIG. 3L-FIG. 3N) Representative TEM images of mitochondrial changes in MCEnCs of mouse corneas without UVA (L, female; magnification: 98,000×) or with 1,000 $J/cm^2$ UVA at 3 mo (FIG. 3M, female, FIG. 3N, male; magnification: 98,000×). The arrowheads indicate the autophagic vacuolar structures in MCEnCs. (Scale bar, 100 nm.)

(FIG. 4A) Schematic illustration of the catechol estrogen metabolic pathway and generation of estrogen-DNA adducts. (FIG. 4B) Representative Western blot of CYP1B1 in normal (n=5) and FECD (n=9) specimens. β-actin serves as normalizing control. Densitometry analysis of the enzyme levels is indicated in the Right as bar graphs. ***$P<0.001$, 2-tailed Student's t test. (FIG. 4C) In vitro Western blotting analysis of CYP1B1 levels in UVA-irradiated immortalized normal CE cells after 7 and 24 h after 5 $J/cm^2$ irradiation (n=3). Treatment with 30 nM TCDD was used as positive control for CYP1B1 induction. Densitometric analysis of CYP1B1 is indicated as bar graph. *$P<0.05$, 2-tailed Student's t test. (FIG. 4D) Western blotting of CYP1B1 levels in the cytoplasmic and mitochondrial fractions extracted from normal CE cells 24 h after 5 $J/cm^2$ irradiation (n=4). Voltage-dependent anion-selective channel (VDAC) and glyceraldehyde 3-phosphate dehydrogenase (GAPDH) served as mitochondrial and cytoplasmic fraction controls, respectively. Densitometric analysis of CYP1B1 normalized to GAPDH (cyto) and VDAC (mito) are indicated as bar graph to the Right. *$P<0.05$, **$P<0.05$, 2-tailed Student's t test. (FIG. 4E) CYP1B1 Western blot in MCEnCs at 1 d after 1,000 $J/cm^2$ UVA. Densitometric analysis of CYP1B1 (n=3 for males, n=4 for females) levels is indicated as bar graphs. *$P<0.05$, 2-tailed Student's t test. (FIG. 4F) Quantitative analysis of 4-$OHE_{1/2}$ levels in the mouse CE 1 d and 3 mo after 1,000 $J/cm^2$ UVA. The accumulation of 4-$OHE_{1/2}$ is represented as the ratio of OD (treated eye) by OS (untreated eye). White and black bars represent WT male (n=6 for 1 d, n=4 for 3 mo) and female (n=7 for 1 d, n=4 for 3 mo) mice, respectively. *$P<0.05$, 2-tailed Student's t test. (FIG. 4G) Ratio of levels of 4-$OCH3E_{1/2}$, 4-quinone conjugates, and 4-$OHE_{1/2}$-DNA adducts 1 d after 1,000 $J/cm^2$ UVA. White and black bars represent WT male (n=7) and female (n=9) mice, respectively. *$P<0.05$, 2-tailed Student's t test. (FIG. 4H) OD/OS ratio of 4-$OHE_{1/2}$, 4-$OCH3E_{1/2}$, 4-quinone conjugates, and 4-$OHE_{1/2}$-DNA adducts in CYP1B1-null mice after ex vivo treatment of corneal cups with 25 $J/cm^2$ UVA. White and black bars represent CYP1B1-null mice male (n=5) and female (n=5), respectively.

(FIG. 5D) Confocal HRT photographs of female or male MCEnC with treatment of 250, 750 or 1000 $J/cm^2$ UVA with NAG at 1 day, 2 weeks, 1, 2 and 3 months post UVA.

(FIG. 6A) Representative in vivo slit lamp images showing mouse corneal clarity (upper row) and fluorescein staining of the corneal epithelial surface (lower row) before UVA and at 1 day, 1 week, 2 weeks, 1, 2 and 3 months post 1000 $J/cm^2$ UVA. (FIG. 6B) Representative phase contrast microcopy images of mouse corneas stained with P&S (FIGS. 6B & FIG. 6C) showing OM thickness in 1000 $J/cm^2$ UVA irradiated mouse corneas and controls (FIG. 6D, data generated from 2 females and 1 male). (FIG. 6E) Representative TEM images of DM of mouse corneas without UVA (F, female, ×18500) and with 1000 $J/cm^2$ UVA (6F, female; 6G, male; ×18500).

(FIG. 7A) Representative confocal images of whole mount of female (upper panels) and male (lower panels) mouse CE with labeling of TUNEL 3 months post 250 or 750 J/cm$^2$ UVA. DAPI was used for nuclei staining. (FIG. 7B) Detection of MCEnC mitochondrial copy number at various time points post 1000 J/cm$^2$ UVA irradiation. LA-qPCR analysis of mtDNA damage (FIG. 7C) and mtDNA copy number (FIG. 7D) in HCEnC-21T cells treated with 4-OHE$_2$ for varying time points. (FIG. 7E) Analysis of DNA lesion frequency in the nDNA encoded β-globin gene in HCEnC-21T cells treated with 4-OHE$_2$ treatment. Data are mean±SEM, *P<0.05 by two-way ANOVA (FIG. 7F) Western Blot of LC3 A/B levels in male and female MCEnCs 1 day post 1000 J/cm$^2$ UVA irradiation.

(FIG. 8A) Western blotting of CYP1A1 levels in both sexes in normal (n=5) and FECD (n=14) ex vivo specimens. β-actin is used as normalizing control. Densitometric analysis of the protein levels is represented as bar graph; black and grey bars denote normal and FECD, respectively. ***P<0.001 by two tailed Students t test. (FIG. 8B) Western blotting of CYP1B1 in both male and female MCEnCs at 3 months post various fluences of UVA irradiation. (FIG. 8C) Western blotting of CYP1A1 levels in male and female MCEnCs 1 day post 1000 J/cm$^2$ UVA. Corresponding densitometric analysis is represented as bar graph to the right. White and black bars denote no UVA and 1000 J/cm$^2$ UVA, respectively. (FIG. 8D) CYP1A1 levels in male and female MCEnCs after 3 months post UVA irradiation with 250, 500, 750 and 1000 J/cm$^2$ doses by western blotting. (FIG. 8E, FIG. 8F) Ratio of OD (treated) by OS (untreated) of 2-OHE$_{1/2}$ generated by CYP1A1 and corresponding 2-DNA adducts in male and female MCEnCs 1 day (E) and 3 months (F) post 1000 J/cm$^2$ UVA.

(FIG. 9A) Western blot of COMT levels in male and female MCEnCs 1 day post 1000 J/cm$^2$ UVA. β-actin serves as normalizing control. (FIG. 9B) COMT levels in male and female MCEnCs after 3 months post UVA irradiation with 250, 500, 750 and 1000 J/cm$^2$ doses by western blotting. OD/OS ratio of levels of 4-OCH3E$_{1/2}$ and 2-OCH3E$_{1/2}$ metabolites generated by COMT in male and female MCEnCs 3 months post 1000 J/cm$^2$ UVA.

(FIG. 13A) Schematic diagram for administration of drug (TMS & vehicle) and time-line for UVA and in vivo imaging (HRT and OCT) in NQO1+/+ and NQO1−/− female mice. (FIG. 13B) In vivo confocal HRT images of NQO1+/+ and NQO1−/− mice treated with Vehicle (DMSO) and TMS (1 mg/kg) at pre-UVA, week 2 and 4 post-UVA (FIG. 13C) Cell density analysis (cell/mm$^2$) of NQO1+/+ and NQO1−/− female mice pre-UVA, and at week 2 and 4 post-UVA and (FIG. 13D) comparison of fold change in corneal endothelial (CE) number (UVA/pre-UVA) of TMS and vehicle treated NQO1+/+ and NQO1−/− mice at week 2 and 4 post-UVA (n=5-6 for TMS and vehicle treated NQO1+/+ and NQO1−/− female mice, *p<0.05, One-way Anova with Tukey's post-hoc test).

(FIG. 14A) Schematic diagram for administration of drug (Berberine & vehicle) and timeline for UVA and in vivo imaging (HRT and OCT) in NQO1+/+ and NQO1−/− female mice. (FIG. 14B) In vivo confocal HRT images of NQ01+/+ and NQO1−/− mice treated with vehicle and berberine (10 mg/kg) pre-UVA and at week 2 post-UVA (FIG. 14C) Cell density analysis (cell/mm$^2$) of NQO1+/+ and NQO1−/− female mice pre-UVA, and at week 2 post-UVA and (FIG. 14D) comparison of fold change in corneal endothelial (CE) number (UVA/pre-UVA) of berberine and vehicle treated NQO1+/+ and NQO1−/− mice at week 2 post-UVA (n=3 for berberine and vehicle treated NQO1+/+ and NQO1−/− female mice, * p<0.05, One-way Anova with Tukey's post-hoc test).

DETAILED DESCRIPTION

Figure 1A:
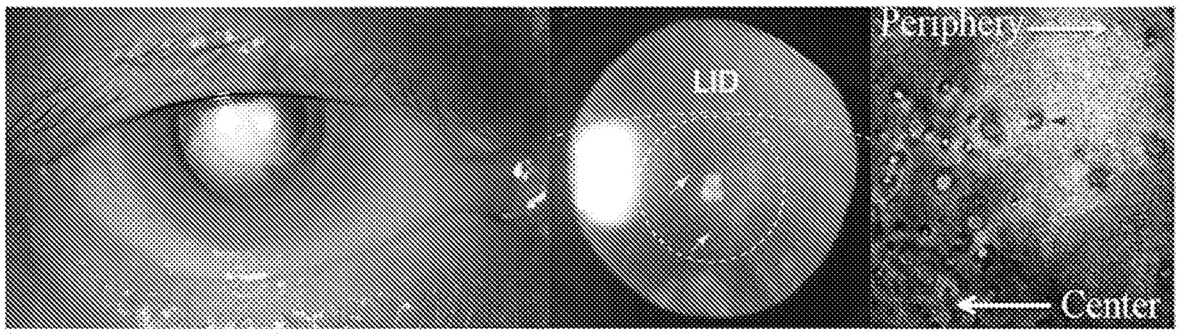
FIGS. 1A-1C. UVA exposure caused progressive MCEnC morphological changes and decreases cell density.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

Methods of Treatment

Corneal endothelium (CE) is a monolayer of cells situated in the anterior chamber surface of the cornea; its primary function is to maintain the cornea in a state of deturgescence through sodium-activated ATPase pumping of water, thus, transparency. Fuchs endothelial corneal dystrophy (FECD) is the most common cause of endogenous corneal endothelial degeneration and is characterized by alterations in corneal endothelial cell morphology, progressive loss of CE cells, and concomitant accumulation of extracellular deposits in the basement membrane that eventually lead to corneal edema and opacity.

Because CE cells do not divide in vivo, loss of endothelial cells seen in FECD is permanent. Corneal transplantation has been the only treatment modality that can restore lost vision-rendering FECD the second most common cause of corneal transplants performed on the elderly (>60 years old) in the U.S. Lack of knowledge of the mechanism of CE degeneration in FECD has precluded the development of pharmacotherapeutics for this common and blinding condition.

FECD has been termed a disorder of aging; it is a bilateral and slowly progressive disorder, typically appearing after the age of 60. FECD is usually a sporadic condition, but it can be inherited as an autosomal dominant trait. FECD is characterized by endothelial cell apoptosis, endothelial cell morphological changes, and concomitant extracellular matrix deposition in the form of mound-shaped excrescences, termed guttae. The loss of CE cells and the formation of guttae start in the central cornea and spread toward the periphery. The number of endothelial cells remaining in the cornea is inversely proportional to the number of guttae excrescences. As the disease progresses, endothelial cell loss is accompanied by the thinning, stretching, and enlargement of neighboring CE cells as well as the loss of their hexagonal shape. Clinically, the endothelial morphological changes in FECD are denoted polymegethism, a variation in cell size, and pleomorphism, a variation in cell shape.

CE may be prone to oxidative stress due to its lifelong exposure to light (the cornea is in the direct light path to the retina), high oxygen demand from exuberant metabolic activity (it has to continually pump ions by Na+K+ATPases), and postmitotic arrest. Proteomic analysis of corneal endothelium taken from patients with FECD and age-matched normal controls has revealed decreased expression of peroxiredoxins (PRDXs), thioredoxin-dependent antioxidants that convert hydrogen peroxide ($H_2O_2$) to water. In addition, increased levels of advanced glycation end products, non enzymatically glycated proteins known to be associated with increased cellular oxidative stress, and their receptors, have been detected in FECD CE and Descemet's membrane compared to normal controls.

The cornea is in the direct path of ultraviolet light (UV) and central cornea receives a substantially greater penetration of UV light compared to the peripheral regions. Specifically, the ultraviolet A (UVA) light (320-400 nm) represents 95% of incident solar radiation, and is absorbed by all layers of the cornea (epithelium, stroma and endothelium). Unlike the shorter wavelength UV8 (280-320 nm)—that directly damages the DNA, UVA causes macromolecular toxicity by photoproduction of reactive oxygen species (ROS). Due to high metabolic activity and post-mitotic arrest, CE is especially susceptible to the damaging effects of UV radiation, indicated by the increased accumulation of (nuclear) oxidative DNA damage and premature senescence in the central and not peripheral CE in the 'normally' aging corneas.

As used herein, the term "patient" or "subject" refers to members of the animal kingdom including but not limited to human beings and "mammal" refers to all mammals, including, but not limited to human beings.

As used herein, the "treatment" or "treating" a disorder or disorders of the corneal endothelium means administration to a patient by any suitable dosage regimen, procedure and/or administration route of a composition, device or structure with the object of achieving a desirable clinical/medical end-point.

Pharmaceutical Compositions and Methods of Administration

The methods described herein include the use of pharmaceutical compositions comprising an inhibitor of a cytochrome P450 as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include topical administration to the eye (e.g., such as an ointment or eye drops) parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for administration to the eye, parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the pharmaceutical compositions, such as the injectable solutions, are suitable for intraocular or intravitreal injections. In some embodiments, the sterile aqueous solutions that may be suitable as an injectable solution may be modified such that it is suitable for topical administration the eye (e.g. as an ointment or as eye drops). Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. Nanoparticles (1 to 1,000 nm) and microparticles (1 to 1,000 μm), e.g., nanospheres and microspheres and nanocapsules and microcapsules, can also be used. These can be prepared according to methods known to those skilled in the art, for example, as described in U.S. Pat. No. 4,522,811; Bourges et al., *Ocular drug delivery targeting the retina and retinal pigment epithelium using polylactide nanoparticles*. Invest Opth Vis Sci 44:3562-9 (2003); Bourges et al., *Intraocular implants for extended drug delivery: therapeutic applications*. Adv Drug Deliv Rev 58:1182-1202 (2006); Ghate et al., *Ocular drug delivery*. Expert Opin Drug Deliv 3:275-87 (2006); and Short, *Safety Evaluation of Ocular Drug Delivery Formulations: Techniques and Practical Considerations*. Toxicol Pathol 36(1):49-62 (2008).

In some embodiments, compositions comprising an inhibitor of a Cytochromes P450. Cytochromes P450 (CYPs) are a superfamily of enzymes containing heme as a cofactor that function as monooxygenases In mammals, these proteins oxidize steroids, fatty acids, and xenobiotics, and are important for the clearance of various compounds, as well as for hormone synthesis and breakdown. In plants, these proteins are important for the biosynthesis of defensive compounds, fatty acids, and hormones.

CYPs are, in general, the terminal oxidase enzymes in electron transfer chains, broadly categorized as P450-containing systems. The term "P450" is derived from the spectrophotometric peak at the wavelength of the absorption maximum of the enzyme (450 nm) when it is in the reduced state and complexed with carbon monoxide. Most CYPs require a protein partner to deliver one or more electrons to reduce the iron (and eventually molecular oxygen).

EXAMPLES

The invention is further described in the following examples, which do not limit the scope of the invention described in the claims.

Example 1

The role of UV light in causing DNA damage and endothelial cell degeneration in FECD has not been explored. Specifically, the temporal effect of UV light-induced mtDNA and nDNA oxidative damage on the functioning of postmitotic cells in vivo has not been extensively studied.

One of the key characteristics of FECD is its greater prevalence in females. Late-onset FECD has greater incidence in women, at a ratio of 3- to 4:1 (11, 12). Central corneal guttae have been found in up to 9% (12) to 11% (13)

of women while only 3.5% (12) to 7% (13) of men showed similar findings. A higher frequency of more advanced FECD has also been reported in women compared to men (14). Female sex, in addition to age, is the most significant risk factor for advanced FECD development (15). A possible hormonal role has been postulated to account for the increased incidence and more severe phenotypic expression of FECD in females (16); however, no definitive studies have been reported. Impaired endogenous estrogen metabolism has been associated with increased breast cancer risk due to cytochrome P450 (CYP)1B1 (CYP1B1)-mediated oxidation of estrogens to reactive quinones, which cause DNA damage (17, 18). CYP1B1 is a member of the CYP family and is expressed in adult tissues (19). It catalyzes the 4-hydroxylation of estrone (E1) and estradiol (E2) into catechol estrogens [4-OHE1(E2)], favoring estrogen quinone [E1(E2)-3,4-Q] formation. The quinones, in turn, react with DNA and form depurinating DNA adducts and apurinic sites in DNA (see FIG. 4A) (17, 18). In addition, there are sex differences in the CYP isoform expression levels, and CYP1B1 is highly expressed in estrogen-related tissues in females (19, 20). For this purpose, we further explored the mechanism of UV-based induction of estrogen metabolism and subsequent DNA damage and how it contributes to the increased incidence and severity of FECD in females.

In this study, we exploited the transparent property of the cornea and created an in vivo model that provides direct visualization of the cellular behavior in response to UV light, as determined by in vivo confocal microscopy and optical coherence tomography (OCT), monitoring the swelling of the cornea as a function of endothelial cell number and morphology. Moreover, we correlated the cellular findings with macromolecular damage (nDNA and mtDNA damage) at different time points of endothelial cell degeneration. Interestingly, our study detected that UVA, the most physiologically relevant light transmitted into the eye (5), leads to phenotypic and molecular changes consistent with FECD. Interestingly, female mice preferentially developed symptoms at low dose UVA, mimicking the status of female human patients, which comprise 75% of the patients undergoing corneal transplantation. We identified the involvement of CYP1B1, the key estrogen-metabolizing enzyme, in sex-dependent differences in CE susceptibility to UVA and detected greater mtDNA damage and estrogen-DNA adduct formation in more severely affected female mice. This study explored the role of UVA in causing DNA damage and activating the estrogen genotoxic pathway in the CE in vivo.

Materials and Methods

Experimental Animals. C57BL/6 wild-type mice (male and female, 7 to 15 wk old; The Jackson Laboratory or Charles River) were used for this study. Mice were housed in a climate-controlled animal facility at the Schepens Eye Research Institute (Boston) and kept under cyclic light conditions with 12 h ON or OFF. Mice were anesthetized with a combined dose of ketamine (100 mg/kg) and xylazine (20 mg/kg) administered intraperitoneally. Female mice were irradiated at proestrus stage (61). For the NAC-treated group, mice were fed daily with drinking water containing 1 g of NAC/kg body weight from 1 d prior up to 3 mo post-UVA. All animal experiments were approved by the Institutional Animal Care and Use Committee and adhered to the ARVO Statement for the Use of Animals in Ophthalmic and Vision Research.

Human Corneal Endothelial Cell Culture. Telomerase and SV40 T antigen immortalized normal human CE cell lines HCEnC-21T and HCEnC-SV-67F-16, respectively, were previously generated in our laboratory (26, 62). HCEnC-21T cells were seeded in estrogen-free medium (phenol red-free OptiMEM-I; Thermo Fisher Scientific) with charcoal stripped FBS (HyClone), 200 mg/L calcium chloride (Sigma-Aldrich), 0.08% chondroitin sulfate (Sigma-Aldrich) and treated with 15 μM 4-$OHE_2$ (Steraloids) in phenol red-free OptiMEM-I. UVA Irradiation of Mouse Cornea. A UVA LED light source (M365LP1; Thorlabs) with an emission peak of 365 nm light, 9 nm bandwidth (FWHM) and irradiance of 398 mW/cm 2 was focused to illuminate a 4-mm-diameter spot onto the mouse cornea. The energy was measured using a laser sensor (model L49 [150A]; Ophir), and the time of UVA exposure was adjusted to deliver the appropriate fluence (10 min 29 s for 250 J/$cm^2$, 20 min 57 s for 500 J/$cm^2$, 31 min 26 s for 750 J/$cm^2$, and 41 min 54 s for 1,000 J/$cm^2$). The right eye (OD) was irradiated while the contralateral eye (OS) was covered with heat retention drapes (SpaceDrapes, Inc.) to serve as untreated control. Mouse eyeballs from CYP1B1-null mice (age 8 to 12 wk, 10 females and 10 males) (31) were enucleated, rinsed with phosphate-buffered saline (PBS), and transported on ice, and cornea excision was performed within 24 h of the animal's death. Four 12-inch RPR-3500A UVA tubes (The Southern New England UV Co.) emitting 350 nm light (irradiance: 7.13 mW/cm 2) were used to irradiate the corneoscleral buttons placed in sterile PBS, with the endothelial side facing the source. The fluence delivered was 25 J/$cm^2$ (58 min 24 s at a distance of 10 cm). Irradiated corneas were snap-frozen, homogenized using a tissue grinder, and dissolved in methanol:water (2:1) for estrogen metabolite analysis.

UVA Irradiation of CE Cell Lines In Vitro. Two 19.5-inch UVA tubes (XX-15L; Analytik Jena US LLC) emitting 365 nm light (irradiance: 14.77 mW/cm 2) were used to irradiate normal CE cells in 12-well cell culture plates in estrogen-free Chens medium. The fluence delivered was 5 J/$cm^2$ (5 min 33 s at a distance of 10 cm from the light source). After irradiation, cells were allowed to recover in the same medium and harvested at 7 h and 24 h.

In vivo Imaging. After anesthetizing, mouse corneal images were taken using a slit-lamp biomicroscope with a camera (Nikon D100, Tokyo). Fluorescein (1 μL in 2.5% in PBS; Sigma-Aldrich) was topically applied onto the mice lateral conjunctival sac to assess the epithelial cell integrity by observing punctate staining under cobalt blue light. Anterior segment images were taken using anterior segment—optical coherence tomography (OCT) (Bioptigen Spectral Domain Ophthalmic Imaging System Envisu R2200 with 12 mm telecentric lens to scan the cornea; Bioptigen). CCT was measured using inbuilt software.

The mouse was wrapped with heat retention drapes on the platform that holds the mouse body securely for imaging CE cells by laser scanning IVCM using the Heidelberg Retina Tomograph III (HRT III) with Rostock Corneal Module (RCM) (Heidelberg Engineering). The laser confocal microscope acquires 2D images that represent a coronal section of the cornea of 400×400 μm (160,000 $\mu m^2$) at a selectable corneal depth. Acquired images comprise 384×384 pixels and with a lateral resolution of 1 μm per pixel. Digital images were stored on a computer workstation at 3 frames per second.

Analysis of CE Cell Density. The CE density of HRT images acquired before UVA and post-UVA at 2 wk and 1 and 2 mo was analyzed by a semiautomated cell counter in the software Heidelberg Eye Explorer, version 1.3.0 (Heidelberg Engineering GmbH) inbuilt in HRT3. The mean cell density was calculated from 3 mice whose HRT images were counted by at least 2 observers. For each image, an area with at least 50 cells was selected. For CE density calculated from the images of 3 mice with ZO-1 immunostaining, cell count was performed manually by 2 blinded observers using a plug-in for ImageJ 1.46r (https://imagescience.org/meijering/software/imagescience; provided in the public domain by Wayne Rasband, NIH). Cell density was normalized to the area of each image in square millimeters.

Analysis of CE Morphology. CE images captured from whole mount ZO-1 immunostaining and uploaded into Confoscan 4 software (NIDEK Technologies, Padua, Italy). The magnification of confocal ZO-1 images used for Confoscan is 40× with zoom 2. Automatic cell analysis was performed after boundaries of the cells were decided. CE polymegethism (variation in cell size) and pleomorphism (variation in cell shape) were calculated. Mean polymegethism and pleomorphism were calculated from 3 images.

Immunocytochemistry and Histology. A dissected mouse cornea cup was fixed with 70% ethanol (ZO-1) or 4% PFA (TUNEL) for 30 min at room temperature. For ZO-1 staining, the cornea cup was permeabilized with 0.2% Triton X-100 in PBS for 10 min and blocked in 2% bovine serum albumin (BSA)-PBS for 15 to 30 min. The cornea cup was incubated with anti-ZO-1 antibody (339100; Thermo Fisher Scientific) in 4% BSA-PBS at 4° C. overnight and with secondary anti-rabbit fluorescein isothiocyanate (FITC) or anti-goat FITC (AB 2315776 or AB 2340401; Jackson Immunoresearch Labs) for 1 h. For the TUNEL assay, an In Situ Cell Death Detection Kit (Roche Diagnostics GmbH) was used according to the manufacturer's instructions. A corneal cup was incubated with TUNEL for 1 h at 37° C. followed by 4 washes with PBS, 10 min each. The corneal cup was flattened by 3 to 4 radial cuts and mounted using DAPI mounting medium (H-1200; Vector Labs). For 8-OHdG-immunostaining, the eyeballs were enucleated and fixed in 10% formalin, embedded in paraffin, sectioned, and stained with anti-8-OHdG (AB5830; Millipore Sigma) overnight at 4° C. and with secondary antibody anti-goat FITC for 1 h. Digital images were obtained using a spectral photometric confocal microscope (DM6000S with LCS 1.3.1 software; Leica). ZO-1-based cell count and TUNEL positive cells were counted by blinded observers using the plug-in for ImageJ 1.46r (https://imagescience.org/meijering/software/imagescience; provided in the public domain by Wayne Rasband, NIH, Bethesda, MD).

ROS Production Assay. Extracellular $H_2O_2$ levels in the mouse aqueous humor (3 μL), collected using a capillary needle from the dilated mouse anterior chamber, were detected using the Amplex Red Assay Kit (Molecular Probes, Life Technologies) according to manufacturer's instructions. Fluorescence was measured with excitation and emission at 550 and 590 nm, respectively, using a microplate reader (Bio-Tek) with Gen5 software at 37° C.

DNA Damage Analysis Using LA-qPCR. Mouse CEs with DM were dissected from a corneal cup and followed by genomic DNA extraction using Qiagen DNeasy Blood and Tissue Kit (Qiagen). LA-qPCR analysis for mtDNA and nDNA was performed as previously described (24). Genomic DNA was isolated from HCEnC-21T cells treated with 4-$OHE_2$ using Genomic tip-20/G (Qiagen). DNA lesion frequencies were calculated as described (24). Two-way analysis of variance (ANOVA) was utilized for statistical analysis, with P values corresponding to <0.05 (*) as significant.

Estrogen Metabolite Analysis. Immediately after euthanizing mice 1 d post-UVA treatment, the corneal cups were dissected, followed by storage at −80° C. Two corneal cups with the same sex and treatment were pooled into one. Frozen corneal cups (2 each) were ground using liquid nitrogen and extracted with methanol/water (1:1, 3×). Fractions were pooled and concentrated using Speed-Vac and lyophilized. The residue was resuspended in 70 μL of methanol/water 1:1 with 0.1% formic acid and filtered through a 5,000-molecular weight cutoff filter (Millipore) before analysis by ultraperformance liquid chromatography/tandem mass spectrometry (UPLC/MS/MS).

All of the samples were analyzed on a Waters Acquity UPLC equipped with a MicroMass QuattroMicro triple stage quadrupole mass spectrometer (UPLC/MS/MS; Waters). The 10-μL injections were carried out on a Waters Acquity UPLC BEHC18 column (1.7 μm, 10×100 mm). The instrument was operated in positive electrospray ionization mode. All aspects of system operation, data acquisition, and processing were controlled using QuanLynx v4.2 software (Waters). The column was eluted starting with 20% acetonitrile in water (0.1% formic acid) for 4 min at a flow rate of 150 μL/min, then to 55% acetonitrile in 10 min. Ionization was achieved using the following settings: capillary voltage 3 kV; cone voltage 15 to 40 V; source block temperature 120° C.; desolvation temperature 200° C., with a nitrogen flow of 700 L/h. Fivepoint calibration curves were run for each standard, and data were quantified by comparison with known amounts of standards as described previously (63). The results were compared between groups using Student's t test.

Materials and Methods for Supplementary Materials

Experimental Animals. Ophthalmic examinations were performed one day prior and 1 day, 1 week, 2 weeks, 1, 2 and 3 months post UVA. Mouse estrous cycle was examined daily by visual vaginal observation at least 5 days before UVA irradiation. Female mice were irradiated at proestrus stage.

UVA lamp Assembly. We developed a customized experimental set up to irradiate the mouse eye in a controlled fashion with varying doses of UVA light. The assembly consists of a UVA LED light source (M365LP1, Thorlabs) producing 365 nm light and an LED driver (LEDD1 B-T cube, Thorlabs) that modulates the current passing through it. Two lenses are employed in this set up. The beam of light from the source passes through the primary converging biconvex quartz lens (15 mm diameter and 8 mm focal length), placed close to the light source, which is further converged by the second fused quartz biconvex lens (1 inch diameter and 20 mm focal length) onto a 4 mm focal spot on the mouse cornea. All components are positioned collinearly on an aluminium base and fixed using supporting steel posts. The irradiation time (s) was calculated by multiplying the irradiance ($W/cm^2$) of the UVA source by the required irradiation dose ($J/cm^2$).

In vivo imaging. Anesthetized mice were restrained inside a DecapiCone holder during the imaging procedures.

In vivo Confocal Microscopy. The mouse was wrapped with heat retention drapes (SpaceDrapes) on the platform that holds the mouse body securely for imaging CE cells by laser scanning IVCM using the Heidelberg Retina Tomograph III (HRT III) with Rostock Corneal Module (RCM) (Heidelberg Engineering, Germany). HRT III RCM is equipped with a 670-nm wavelength diode laser source and 63× objective immersion lens with a numerical aperture of 0.9 (Olympus, Tokyo). For each eye examination, a disposable sterile polymethylmethacrylate cap (Tomo-Cap; Heidelberg Engineering GmbH) filled with a drop of GenTeal gel eye ointment (hydroxypropyl methylcellulose 2.5% Novartis Ophthalmics, NJ) in the bottom was mounted in front of the cornea module optics. A drop of GenTeal gel was placed both on the eye and the tip of the objective lens to maintain immersion contact. During acquisition of images, the central cornea was made to focus on the instrument's red light fixation that was moved until the eye was in the imaging axis of RCM. The RCM objective lens was manually moved until the CE cells were in focus. The images were captured by scan mode of volume, sequence or section. The laser confocal microscope acquires 2D-images that represent a coronal section of the cornea of 400×400 μm (160,000 $\mu m^2$) at a selectable corneal depth. Acquired images comprises 384×384 pixels and with a lateral resolution of 1 μm/pixel. Digital images were stored on a computer workstation at three frames per second.

Transmission electron microscopy. Mouse eyes were enucleated and immersion fixed with half strength Karnovsky's fixative (2% formaldehyde+2.5% glutaraldehyde, in 0.1 M sodium cacodylate buffer, pH 7.4; Electron Microscopy Sciences, Hatfield, PA) at room temperature followed by dissecting the corneal cups. Corneal cups were placed back into the half strength Karnovsky's fixative for a minimum of 24 h under refrigeration. After fixation, samples were rinsed with 0.1 M sodium cacodylate buffer, post-fixed with 2% osmium tetroxide in 0.1 M sodium cacodylate buffer for 1.5 h, en bloc stained with 2% aqueous uranyl acetate for 30 min, then dehydrated with graded ethyl alcohol solutions, transitioned with propylene oxide and resin infiltrated in tEPON-812 epoxy resin (Tousimis, Rockville, MD) utilizing an automated EMS Lynx 2 EM tissue processor (Electron Microscopy Sciences, Hatfield, PA). Processed tissues were oriented in tEPON-812 epoxy resin and polymerized in silicone molds in an oven set at 60° C. Semi-thin cross-sections for light microscopy were cut at 1 μm and stained with 1% toluidine blue in 1% sodium tetraborate aqueous solution for assessment and screening regions of the tissue block face for thin sectioning. Ultrathin sections (70-90 nm) were cut from the epoxy block using a Leica EM UC7 ultramicrotome (Leica Microsystems, Buffalo Grove, IL) and a diamond knife, collected onto 2×1 mm single slot formvar/carbon coated grids and were stained with aqueous 25% Uranyl Acetate Replacement stain (Electron Microscopy Sciences, Hatfield, PA) and Sato's lead citrate using a modified Hiraoka grid staining system. Grids were imaged using a FEI Tecnai G2 Spirit transmission electron microscope (FEI, Hillsboro, OR) at 80 kV interfaced with an AMT XR41 digital CCD camera (Advanced Microscopy Techniques, Woburn, MA) for digital TIFF file image acquisition. TEM imaging of all layers of the cornea was assessed and images captured at representative regions.

Western Blotting. Mouse CE with DMs were dissected from corneal cup followed by lysis with the protein extraction buffer ER3 (Biorad; Hercules, CA) and 1 mM tributyl phosphine (TSP). Proteins were loaded onto 10% Bis-Tris NuPAGE gels (Invitrogen). Peptides were transferred to a polyvinylidene difluoride (PVDF) membrane (Millipore; Billerica, MA) and non-specific binding was blocked with 5% dry nonfat milk in PBS or 5% BSA in 0.05% Tween20/TBS for 1 h. Membranes were incubated overnight at 4° C. with anti-CYP181 (BD Biosciences #458511), antiCYP1A1 (Abeam, #ab79819), anti-LC3 A/8 (Cell Signaling, #3868), anti-COMT (Cell Signaling, #14368), and anti-NQO-1 (Abcam, #ab2346). anti-β-actin (Sigma-Aldrich, A1978) was used to normalize protein loading. Blots were rinsed, re-blocked, and exposed for 1 h to horseradish peroxidase (HRP)-conjugated goat anti-rabbit IgG for CYP1B1, LC3A/B and COMT and HRP-conjugated donkey anti-mouse IgG for β-actin blots. After washing in 0.05% Tween20/PBS, antibody binding was detected with a chemiluminescent substrate (Thermo Scientific). Densitometry was analyzed with ImageJ software (NIH), and protein content was normalized relative to β-actin.

Mitochondrial fractionation. For assessing the mitochondrial levels of CYP1B1 in UVA treated HCEnC-21T cells, mitochondria were purified using BioVision Mitochondria/Cytosol Fractionation Kit (Cat no-K256-25) according to manufacturer's instructions. The fractions were loaded onto 10% Bis-Tris NuPAGE gels for western blotting as described above. Rabbit polyclonal anti-CYP1B1 (Abcam, #ab185954), VDAC (Abcam, #ab18988) and GAPDH (Sigma, G9545) primary antibodies were used.

Statistical Analysis. Results were expressed as the mean±SE. Data of cell density, hexagonality, coefficient of variation, ROS production, TUNEL labeled apoptotic cells and CYP1B1 levels were analyzed using a two-tailed unpaired Student's t-test. Longitudinal CCT data were analyzed by mixed effect regression analysis (Stata 14, StataCorp LLC, TX). LA-qPCR results were analyzed by two-way analysis of variance with Bonferroni post hoc test (Graphpad Prism 5, Graphpad Software Inc, CA). $P<0.05$ was considered statistically significant.

UVA Irradiation Causes Progressive Alterations in Mouse Corneal Endothelial Cell Morphology and Greater Cell Loss in Females.

The clinical hallmark of FECD is formation of dome-shaped extracellular matrix deposits called guttae (red arrowheads and white arrows, FIG. 1A) and CE cell loss in the central cornea, often sparing in the peripheral cornea or areas covered by eyelids that shield the eye from UV light, as demonstrated by the slit lamp (FIG. 1A, Middle) and In vivo confocal (FIG. 1A, Right) images of the FECD patient cornea (FIG. 1A). This suggests positive correlation of guttae formation and the exposure of UVA in the central cornea. FECD is characterized by a decline in CE cell number and morphological changes manifested by loss of regular hexagonal shape (% hexagonality) and an increase in cell size and shape variability (coefficient of variation). To demonstrate the physiological importance of UVA in FECD pathogenesis, we developed an In vivo UVA-induced late onset FECD mouse model. We established an experimental setup where the right cornea of the mouse eye (OD) was irradiated at 365 nm wavelength with varying doses (250, 500, 750, and 1,000 $J/cm^2$), which delivers peak UVA-induced photon radiation absorbed by the cornea (5). Postirradiation, mouse corneal endothelial cell (MCEnC) morphology and density were assessed by In vivo confocal microscopy (Heidelberg retina tomograph [HRT]) at various time points after irradiation (FIG. 1B and FIG. 5A-D). The mouse CE showed a characteristic hexagonal monolayer with regular size and shape, consistent with the human endothelium (FIGS. 5B and C) (21, 22). UVA induced fluence-dependent disruption of the monolayer, with reduction in cell density from ~2,200 to ~900 cells per square millimeter in a dose- and time-dependent manner within 2 mo postirradiation (FIG. 1C, Right and FIG. 5A-D). Moreover, UVA caused formation of guttaelike lesions where drop-like bright "deposits" were surrounded by dark areas of lost cells (arrowheads, FIG. 1B), comparable with the morphological changes seen in the human FECD cornea (arrowheads, FIG. 1A, Right). Interestingly, we detected sex-dependent differences in MCEnC morphology and cell loss.

Figure 1B:
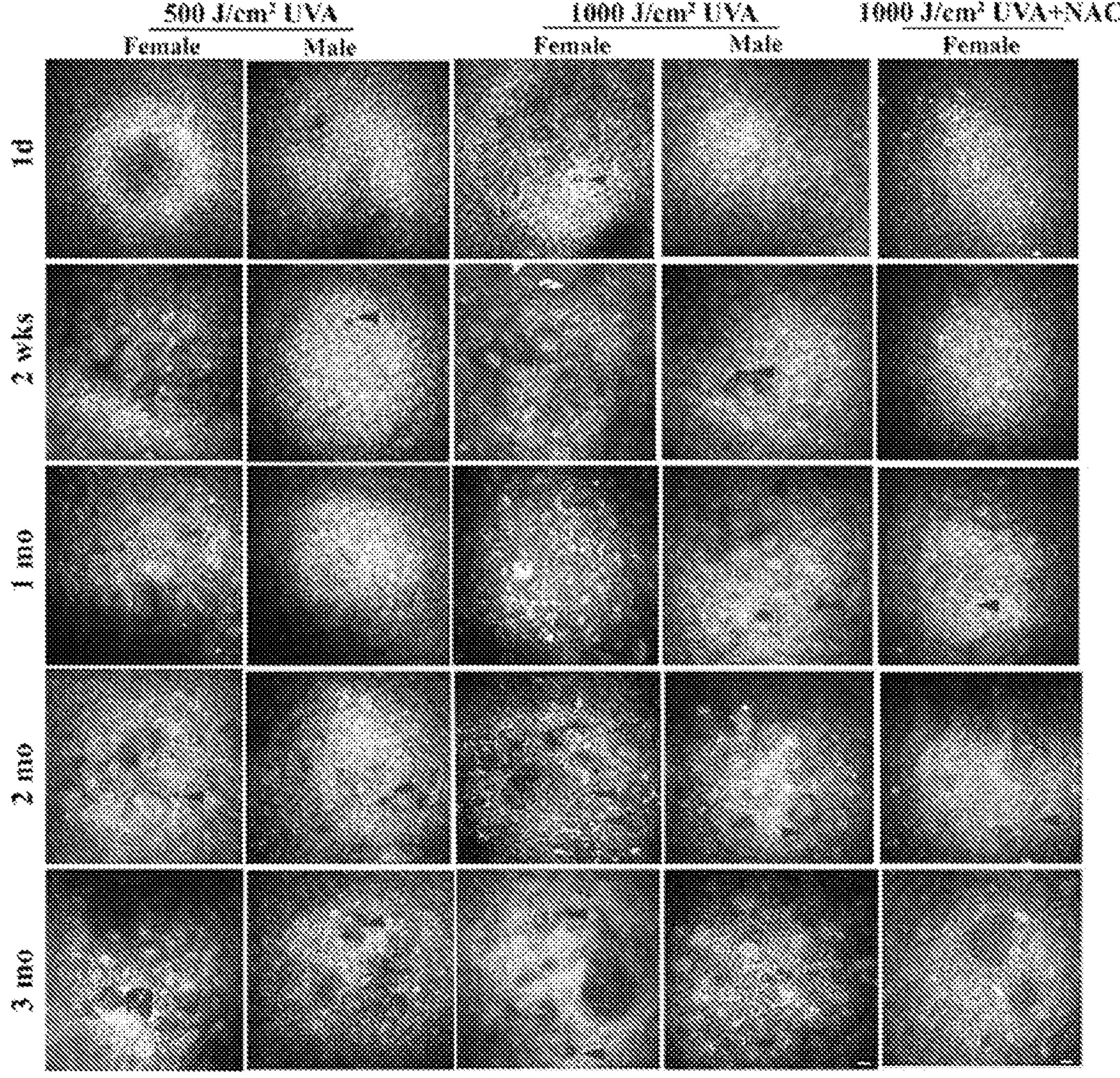
Figure 1C:
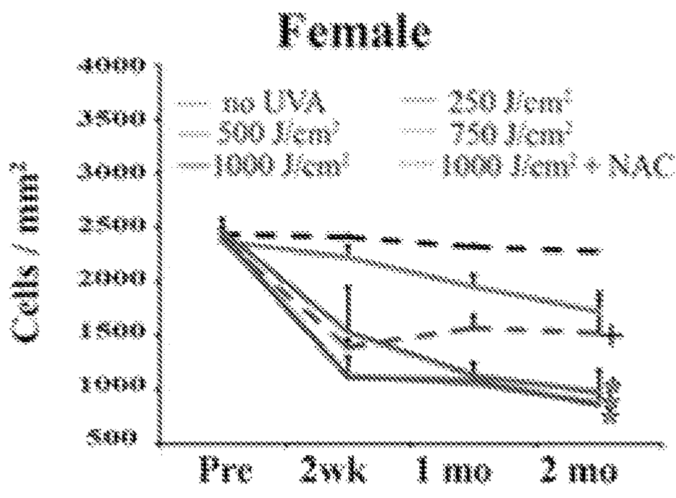
Figure 1C:
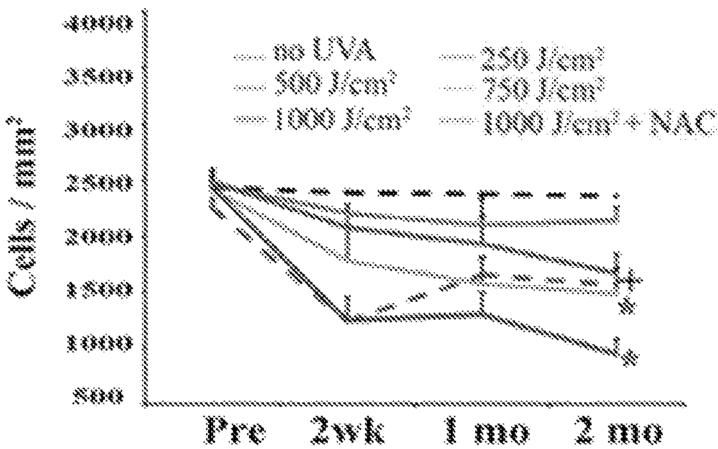
Figure 1C:
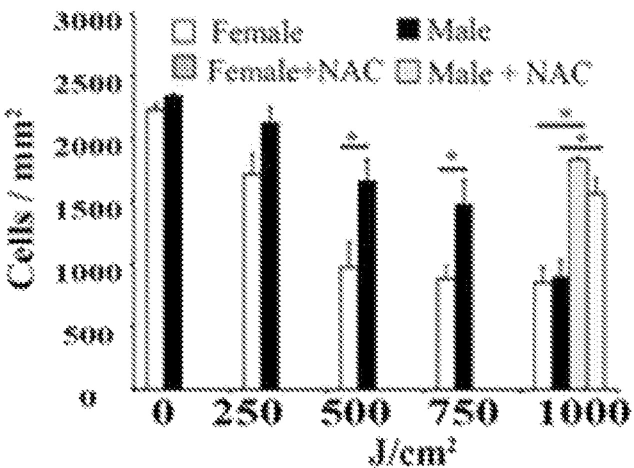
Figure 2A:
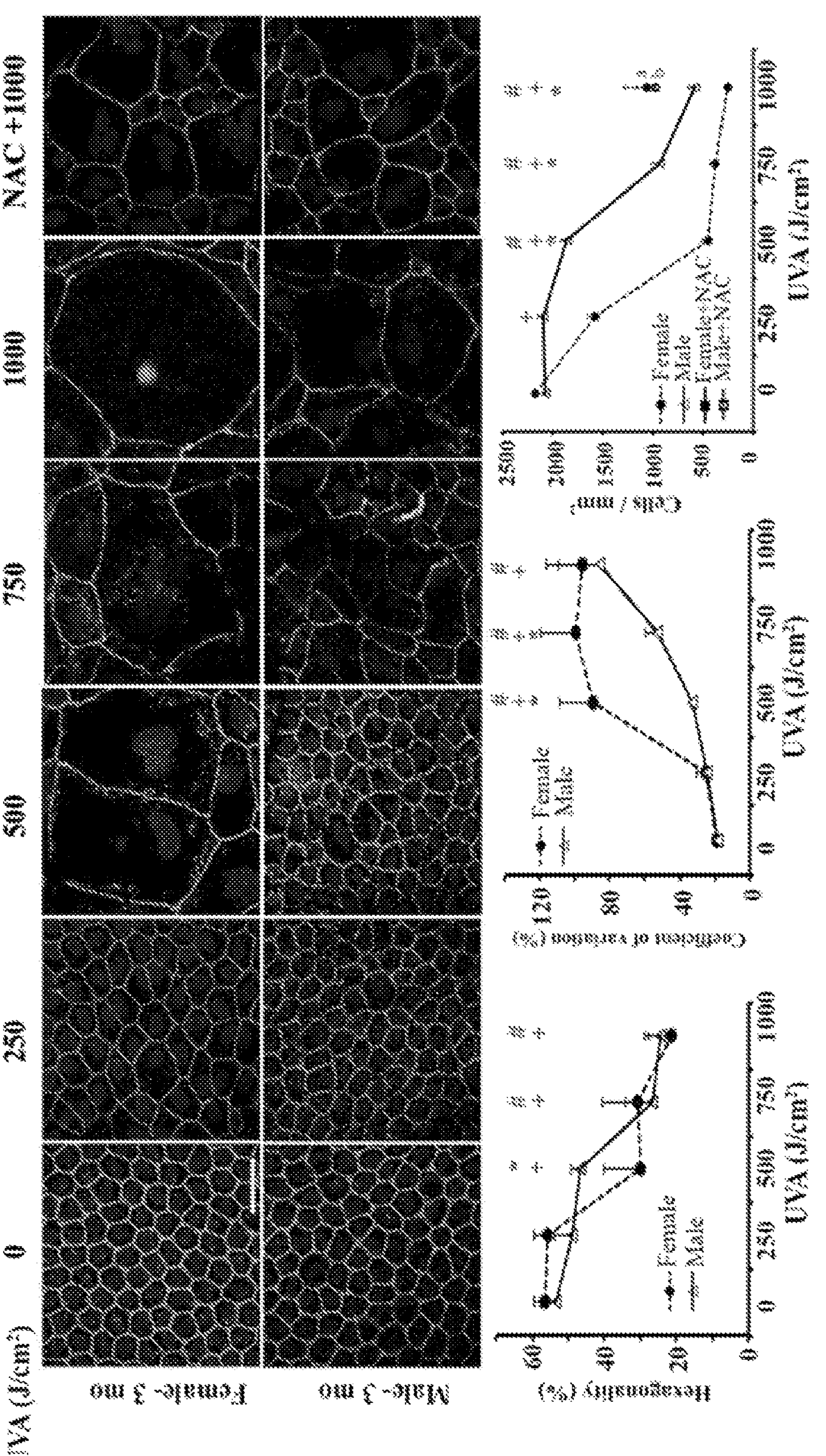
FIGS. 2A-2C. UVA irradiation altered cell size and shape and modulates CCT.
Figure 5:
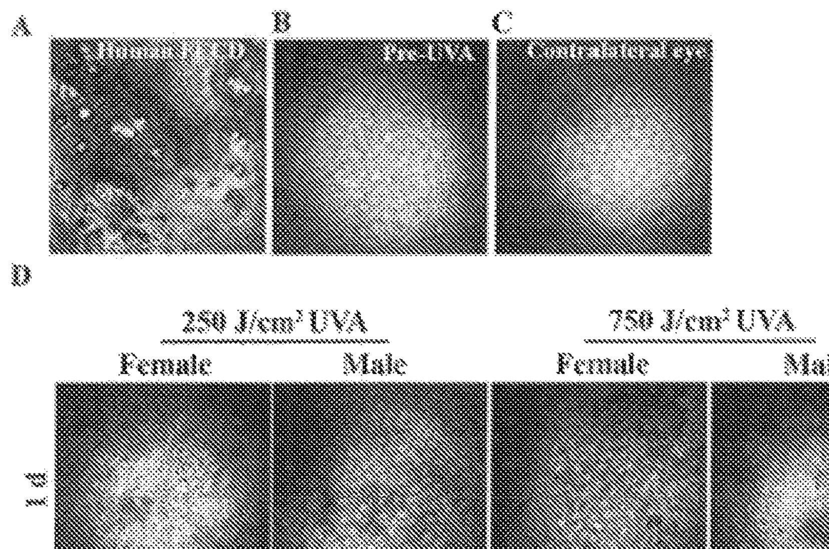
FIGS. 5A-5D. In vivo confocal HRT photographs of CE from FECD patient (FIG. 5A). Arrowheads indicate guttae. MCEnCs before UVA treatment (FIG. 5B) and from the contralateral eye (FIG. 5C) without UVA.
Figure 6:
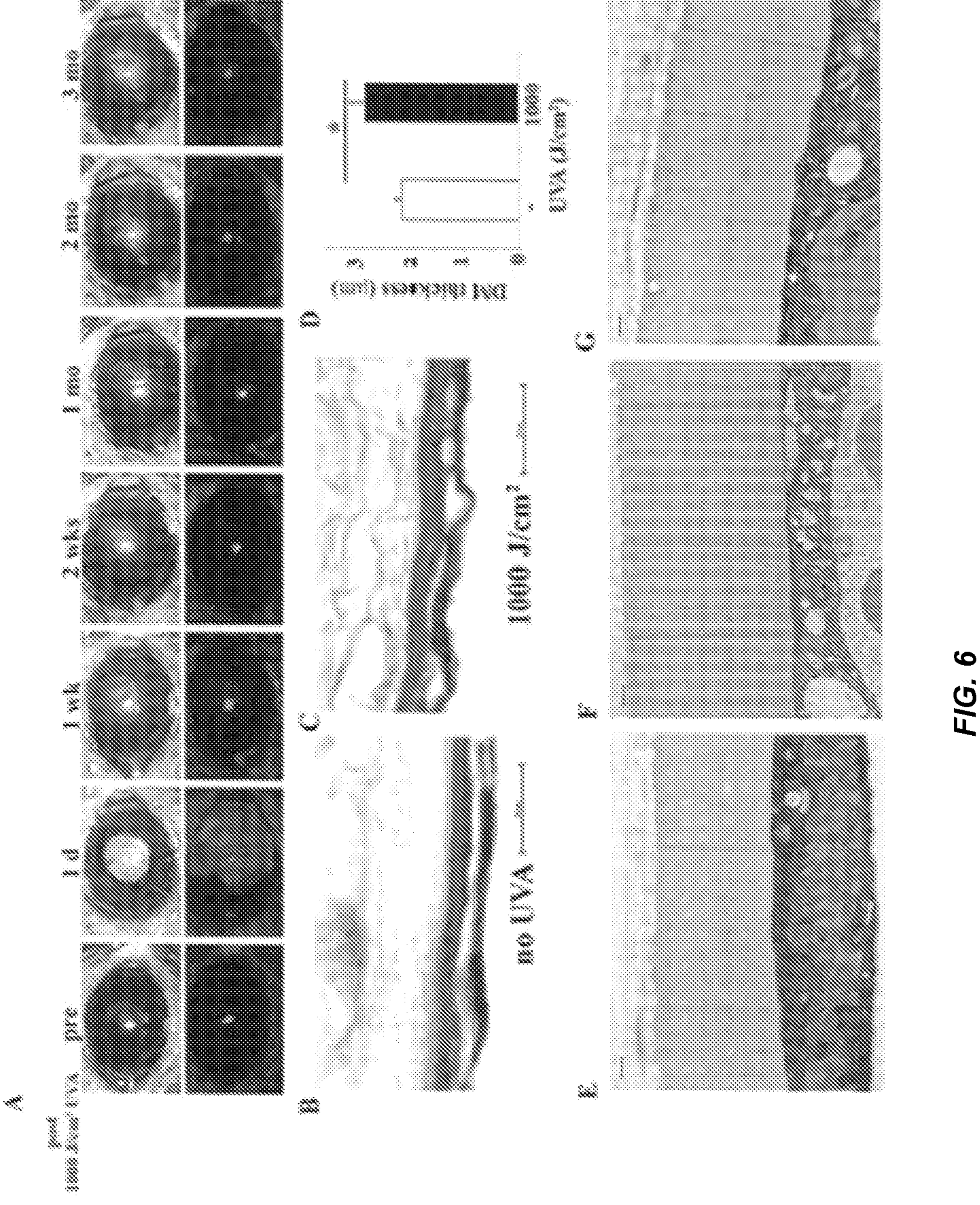
FIGS. 6A-6G.

While females had a sharp decline in the cell density with 500 J/cm$^2$, male mice did not show a significant decrease until 750 J/cm$^2$ at 2 mo compared to preUVA (FIG. 1C). Specifically, female mice showed exacerbated morphological changes, such as increased cell size and loss of discernible cell borders, as compared to males at the same recovery time points (FIG. 1B). After 500 J/cm$^2$, males retained the hexagonal monolayer configuration for up to 2 mo while females showed progressive disruption of the monolayer, with enlarged and irregular cells starting at 2 wk, and continued to display a more severe phenotype than males till a 3-mo time point. Similarly, after 1,000 J/cm$^2$, males showed discernible, although sicker, cells up to a 2-mo time point while females exhibited disorganized mosaic and loss of discernible cell junctions starting at 2 wk. Accordingly, females had 41% and 42% (500 J/cm$^2$) and 33% and 40% (750 J/cm$^2$) lower cell densities than males 1 and 2 mo after UVA, respectively (FIG. 5E and FIG. 1C). At the 3-mo time point, progressive damage to the CE prevented reliable cell counts in vivo; thus, confocal images of tight junctions, immunostained ex vivo, were used for the morphometric analysis (FIG. 2A). After 3 mo, sex-dependent differences were present across all UVA doses, showing a decline in females by 24.5% (250 J/cm$^2$), 75.7% (500 J/cm$^2$), 60% (750 J/cm$^2$), and 57% (1,000 J/cm$^2$) compared to male mice (FIG. 2A, Right Graph). Moreover, the hexagonality was 17% lower in females after 500 J/cm$^2$ (FIG. 2A, Left Graph), and the coefficient of variation was greater by 56.5% (500 J/cm$^2$) and 47.0% (750 J/cm$^2$) in females as compared to males (FIG. 2A, Middle Graph), indicating that females were more susceptible to UVA than male counterparts. N-acetylcysteine (NAC) is an L-cysteine amino acid and a precursor to glutathione (GSH), known for its antioxidant and ROS scavenging properties (23). Since NAC has been shown to be cytoprotective in the COL8A2 mouse model of early-onset FECD (21), we tested the effect of NAC on UVA-induced MCEnC changes mimicking age-related FECD. The mice were fed with NAC 1 d prior to 1,000 J/cm$^2$ UVA irradiation and for 3 mo thereafter. Interestingly, we detected a 1.7-fold increase in MCEnC density in females (1,521±313 for NAC vs. 855±115 for no-NAC) and a 1.6-fold increase in males (1,560±136 for NAC vs. 944±136 for no-NAC) as compared with 1,000 J/cm$^2$ UVA irradiation only at 2 mo (FIG. 1C). Similarly, NAC supplementation significantly rescued both male and female endothelial cell density even at 3 mo after UVA, suggesting that ROS quenching restored UVA-induced cell loss (FIG. 2A).

UVA Irradiation Increases Central Corneal Thickness to a Greater Extent in Females.

Figure 2B:
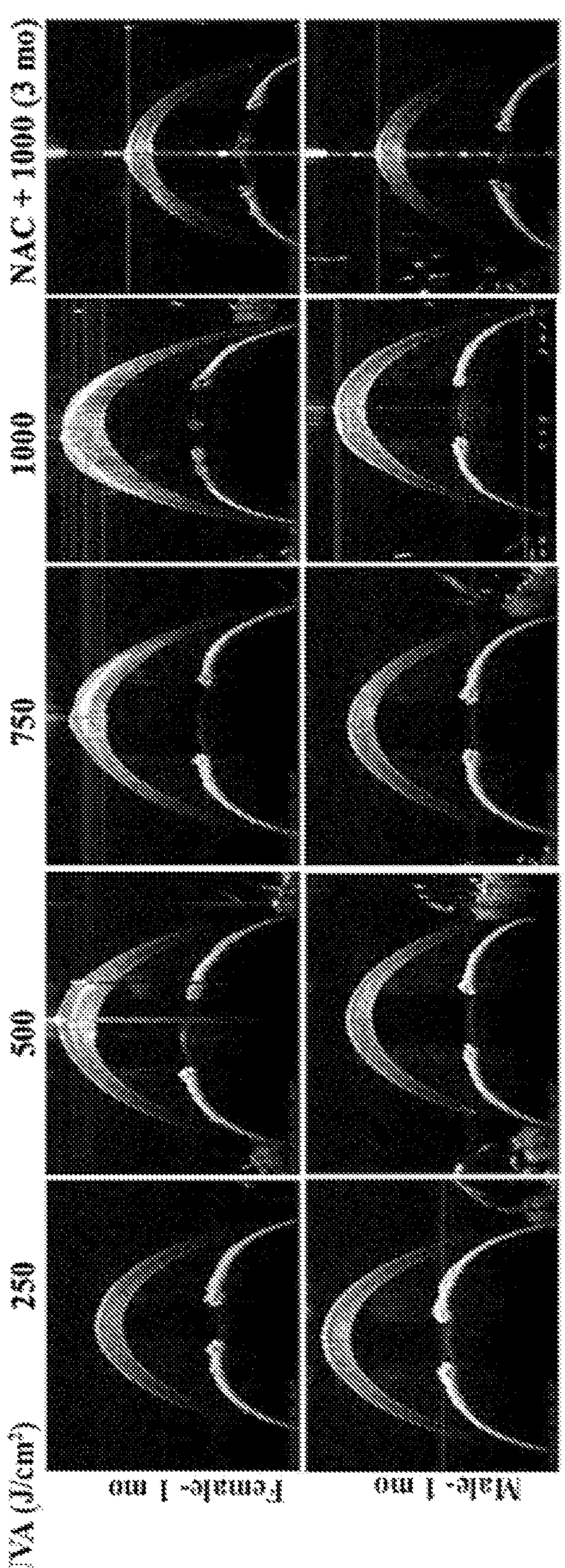
Figure 2C:
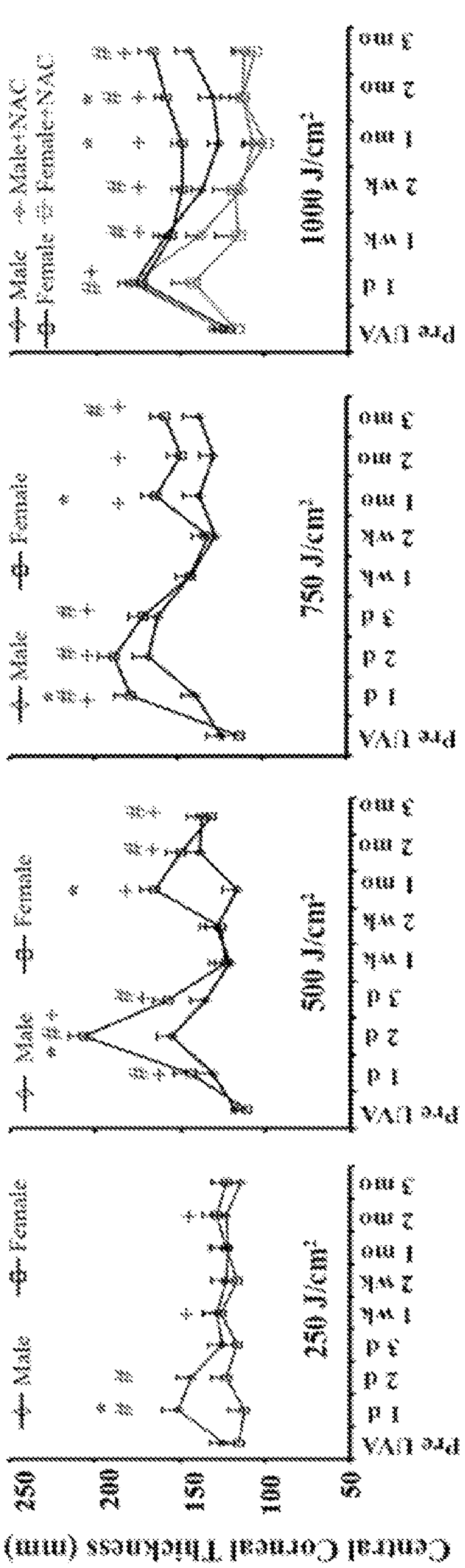

Corneal edema leads to an increase in central corneal thickness (CCT), which is a hallmark of endothelial cell functional impairment. The effect of UVA on MCEnC function was monitored by serial CCT measurements with in vivo OCT. Acutely, UVA irradiation led to the damage of the superficial corneal epithelium, (FIG. 6A), leading to loss of epithelial barrier function and transient increase in CCT, not indicative of endothelial dysfunction. By 1 wk postirradiation, the epithelial defects healed (FIG. 6A), and the CCT normalized to baseline for 500 and 750 J/cm$^2$ doses (FIGS. 2B and C); however, the second peak of CCT increase started at 1 mo after UVA for female mice (FIG. 2B) and at 2 to 3 mo for male mice, indicating the induction of corneal edema (FIG. 2C) as a function of MCEnC loss (FIG. 2A). For the 1,000 J/cm$^2$ dose, even when epithelium healed (FIG. 6A), corneal edema persisted (albeit improved from 1 d) and progressed for up to 3 mo, demonstrating a greater damage to the MCEnC function with a higher dose (FIG. 2C). Similar to the cell density findings (FIG. 2A), we detected a sex-dependent difference in CCT values. Females showed an earlier onset of endothelial function-related edema at 1 mo, with a 1.4-, 1.2-, or 1.2-fold increase in CCT for 500, 750, and 1,000 J/cm$^2$, respectively, compared to males (FIGS. 2B and C). The difference persisted up to a 2-mo time point after 1,000 J/cm$^2$ UVA, until both male and female corneas swelled to the same "maximal" point at 3 mo. Interestingly, the CCT of NAC-treated mice remained close to the untreated baseline at 1 to 3 mo after 1,000 J/cm$^2$ UVA without an induction of the second peak of edema, indicating the protective role of NAC on endothelial function (FIGS. 2B and C). NAC-treated males showed a significant decrease in CCT at 2 wk and 1 and 3 mo, and NAC-treated females showed a significant decrease in CCT at 1, 2, and 3 mo after 1,000 J/cm$^2$ UVA, as compared to 1,000 J/cm$^2$ treated males and females, respectively (FIG. 2C, Right Graph). The histological feature of FECD is the thickening of Descemet's membrane (DM). Periodic acid-Schiff (PAS) staining revealed increased DM thickness from 2.1±0.10 μm to 2.8±0.28 μm and corneal edema at 3 mo after 1,000 J/cm$^2$ UVA (FIG. 6B-F). Similarly, transmission electron microscopy (TEM) images (FIG. 6G-I) showed thicker DM in UVA-treated eye as compared to controls.

UVA Irradiation Induces Oxidative nDNA and mtDNA Damage Augmented in Female Mice.

To determine whether UVA affects the intraocular milieu abutting the CE (effects are ROS-dependent in vivo), we analyzed and compared the ROS production in the mouse and human aqueous humor (FIG. 3A-C). Extracellular $H_2O_2$ levels in the aqueous humor showed a 4- and 11.6-fold increase in females and males, respectively, compared to those in control eyes (FIG. 3A). Furthermore, NAC supplementation significantly reduced ROS formed due to UVA (FIG. 3B). Similarly, aqueous fluid taken from FECD patients exhibited 2-fold heightened $H_2O_2$ levels, indicating a prooxidant milieu impacting FECD pathogenesis (FIG. 3C).

Figure 3E:
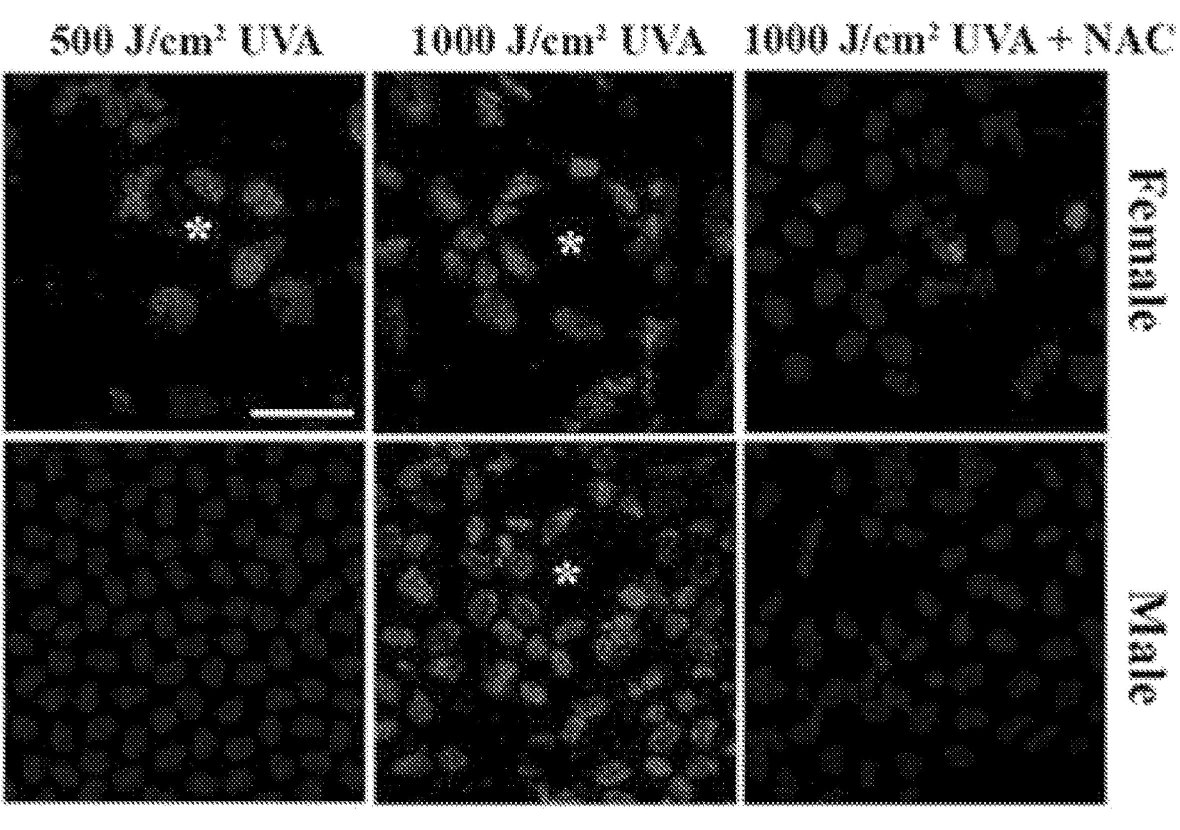
Figure 3F:
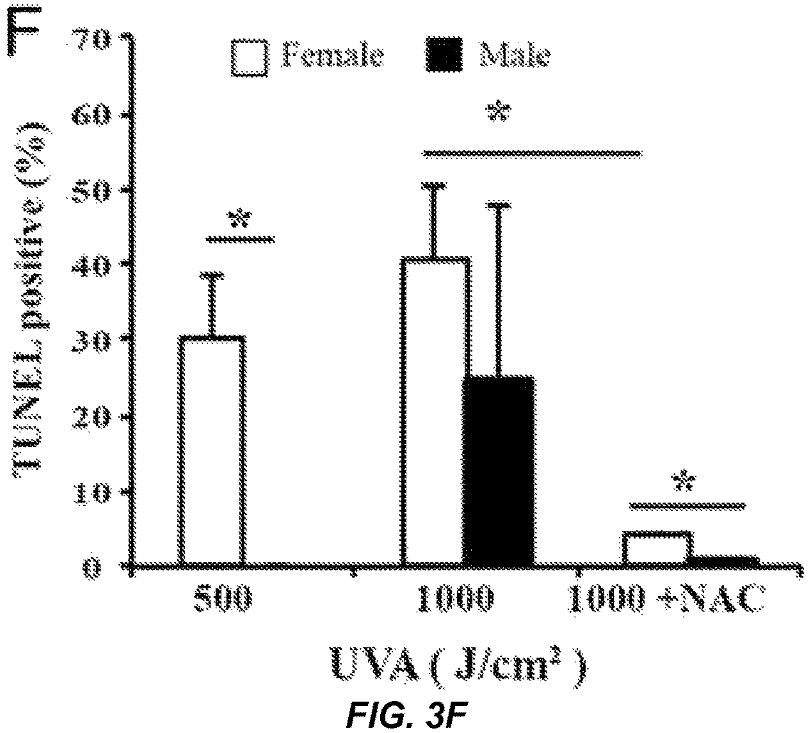
Figure 7:
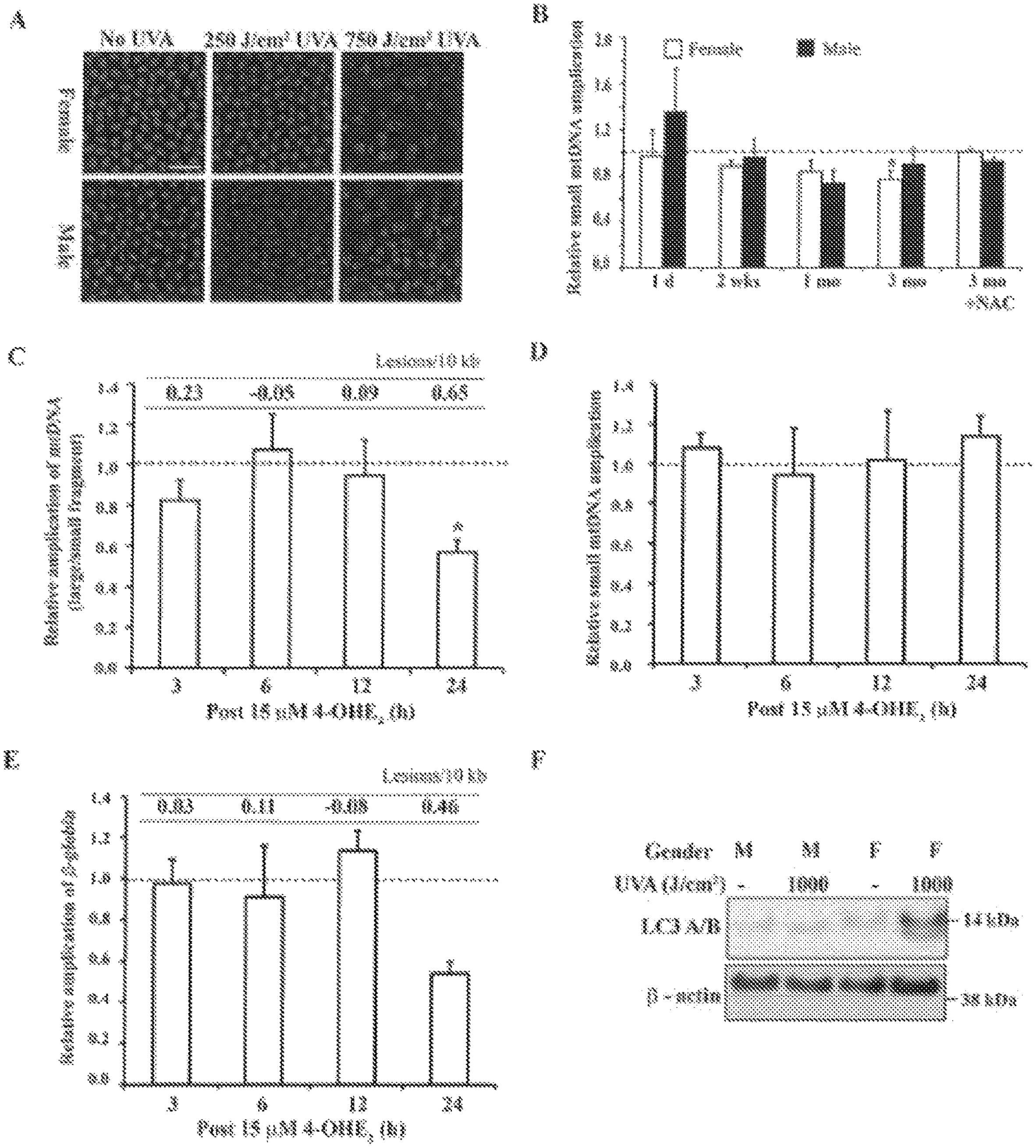
FIGS. 7A-7F.

Furthermore, intense immunostaining with anti-8-OHdG (8-hydroxy-2'-deoxyguanosine), the marker of DNA oxidation, was detected in MCEnCs after UVA, recapitulating the findings of FECD ex vivo (22) (FIG. 3D). At 3 mo post-UVA, a terminal deoxynucleotidyltransferase-mediated dUTP nick end labeling (TUNEL) assay, which detects DNA fragmentation and apoptosis, showed 30% and 40% TUNEL-positive cells after 500 and 1,000 J/cm$^2$, respectively, in female mice while, in male mice, only 1,000 J/cm$^2$ induced TUNEL-positive apoptosis of 24% (FIGS. 3E and F). However, TUNEL-positive cells were not observed upon irradiation with 250 J/cm$^2$ UVA (FIG. 7A). Specifically, UVA induced the formation of rosettes where apoptotic MCEnCs clustered around spaces of missing cells, similar to the pattern seen in FECD ex vivo. NAC-treated females and males showed significantly less TUNEL-positive cells as compared to non-NAC-treated UVA irradiated mice while NAC-treated males had fewer TUNEL-positive cells compared to NAC-treated females (FIG. 3E).

Figure 3G:
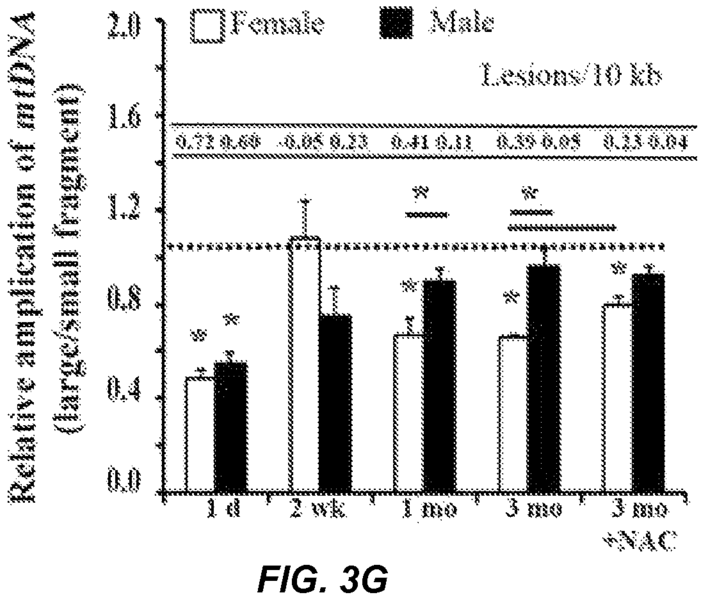

Next, we hypothesized that a differential response to the DNA damaging effects of UVA light might explain the sex-differences in the FECD phenotype. To test this, we performed long-amplicon PCR (LA-qPCR) analysis (24) (investigating the extent of nDNA and mtDNA damage) of MCEnCs during the FECD-phenotype development and compared the findings between female and male mice. The untreated contralateral eyes served as controls. The relative amplification of the small mtDNA fragment was employed as an estimate of mtDNA copy number (FIG. 7B) UVA induced immediate mtDNA damage by decreasing amplification of mtDNA by 51% and 49% in female and male MCEnCs at 1 d, respectively (FIGS. 3G and J). The mtDNA damage recovered at a 2-wk time point for both sexes and then showed a second peak of damage, but only in females. Female mice exhibited a decrease in mtDNA amplification and an increase in lesion frequency at 1 mo (by 33%) and 3 mo (by 34%), demonstrating a 3.8- and 8.2-fold increase in mtDNA lesions per 10 kb compared to males at 1 and 3 mo, respectively. This suggested a secondary macromolecular damage occurring after the repair of the initial insult in females and not males.

Figure 3H:
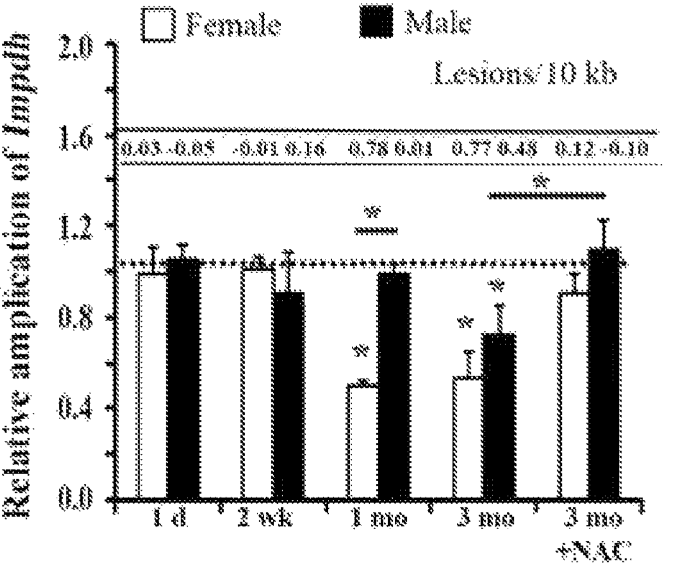
Figure 3I:
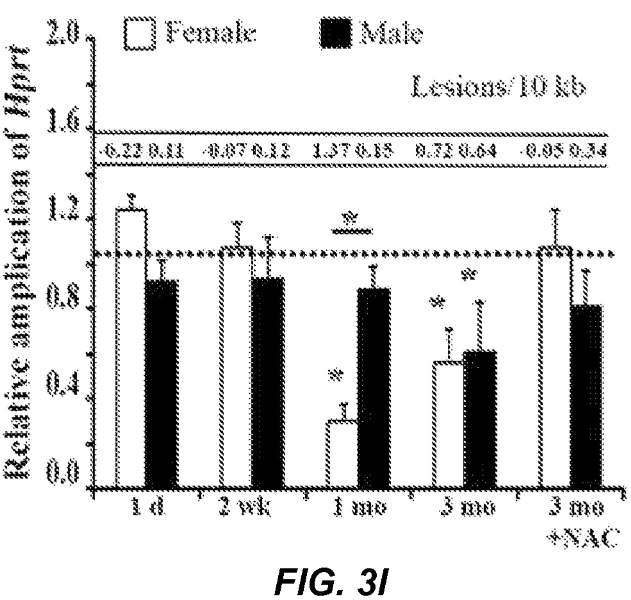
Figures 3J, 3K:
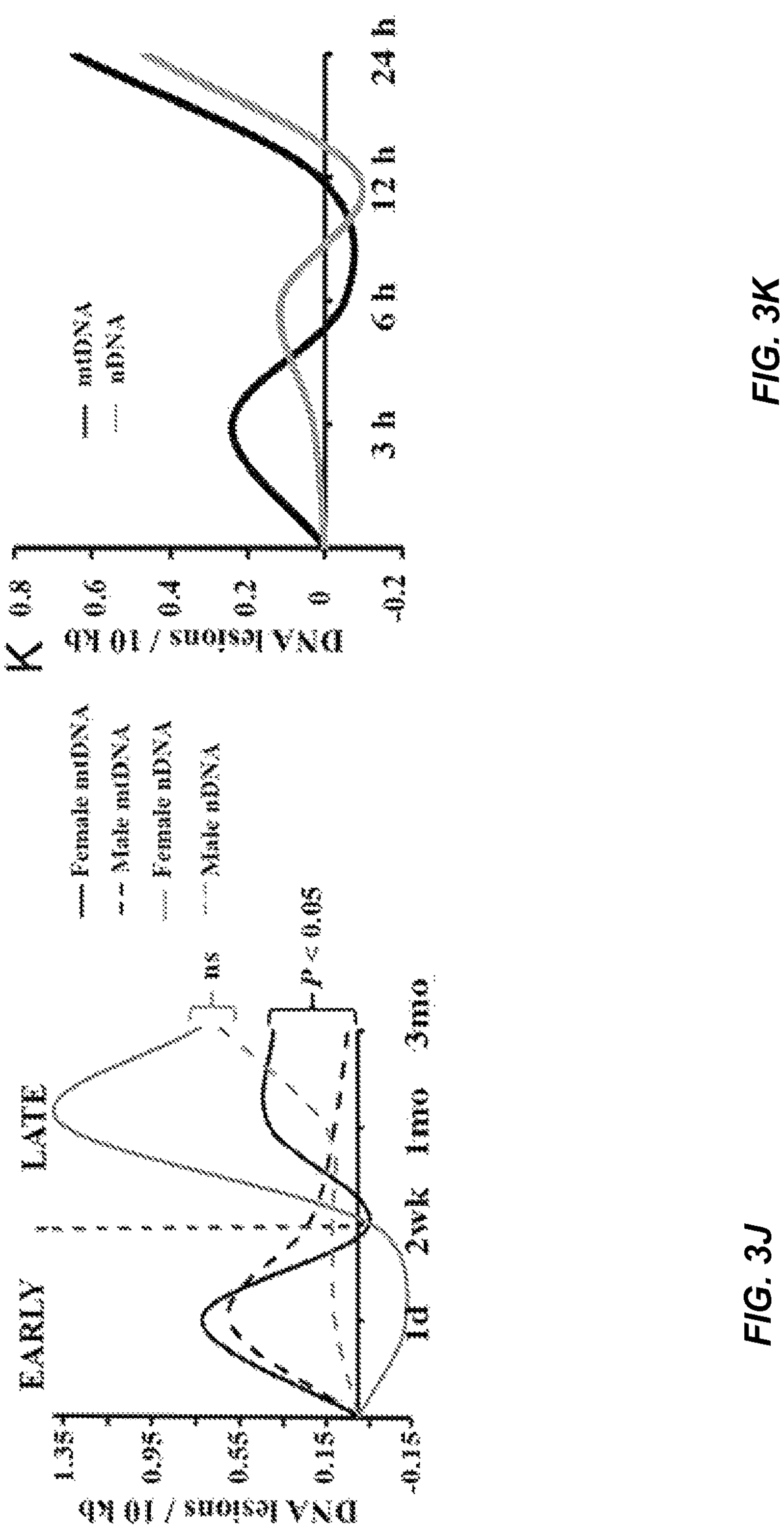
(FIG. 3J) Graphical representation of the mtDNA (black) and nDNA lesions (gray) in female (solid line) and male (dashed line) MCEnCs from 1 d to 3 mo after 1,000 $J/cm^2$ UVA. "ns" indicates nonsignificant.
(FIG. 3K) Graphical illustration of the mtDNA (black) and nDNA lesions (gray) in normal HCEnC-21T cells upon 15 μM 4-$OHE_2$ treatment for varying time points.

The analysis of nDNA loci revealed that UVA induced a "delayed" damage starting only at the 1-mo time point where reduction in amplification of Impdh (by 49.7%, 0.78 lesions per 10 kb) and Hprt (by 70.5%, 1.37 lesions per 10 kb) occurred only in females (FIGS. 3H-J). At 3 mo post-UVA, amplification of Impdh reduced by 46.7% in females and by 27.5% in males. Similarly, amplification of Hprt declined by 44.3% in females and 40% for males. No nDNA sex differences were observed at 3 mo. However, with 1,000 J/cm$^2$ UVA at 3 mo, NAC treatment significantly rescued the nDNA damage in both sexes while mtDNA damage in females persisted even after NAC treatment (FIGS. 3G-I). Further, we sought to recapitulate the mtDNA damage noted in female mice in the immortalized human normal CE cell line (HCEnC-21T). We treated HCEnC-21T cells with the catechol estrogen 4-hydroxyestradiol (4-OHE$_2$) to mimic the female milieu in cells. We noted increased mtDNA lesions (0.65 DNA lesions per 10 kb) in HCEnC-21T cells at 24 h in comparison with 0.46 DNA lesions per 10 kb in the nuclear encoded β-globin gene (FIG. 3K and FIG. 7C-E).

Figure 3N:
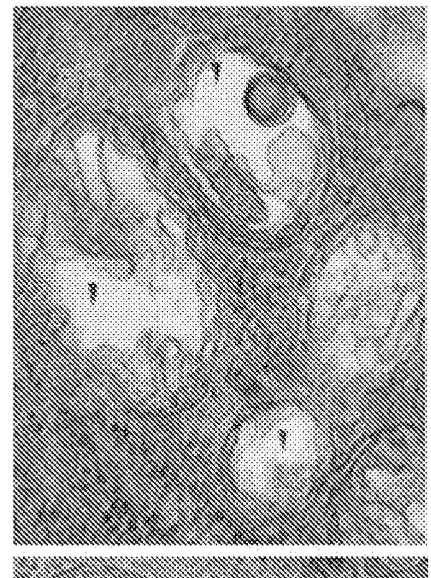
Figure 3M:
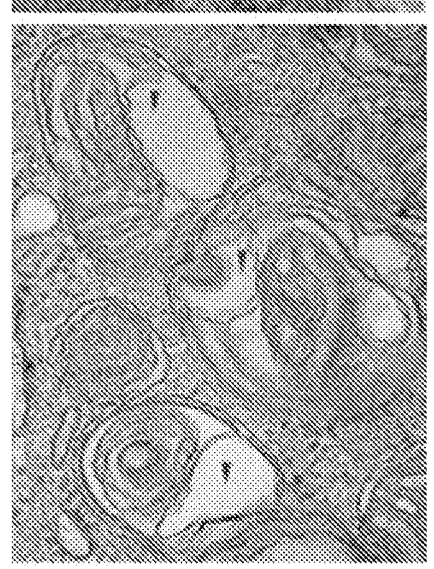
Figure 3L:
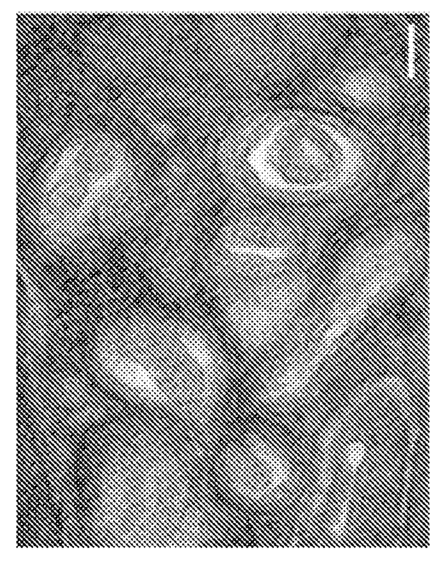

To rule out the possibility that mtDNA damage is due to impaired mitophagy where lack of clearance of dysfunctional mitochondria leads to persistent DNA damage, we performed ultrastructural analysis of MCEnCs (25). TEM showed an increase in the number and size of vacuoles containing mitochondria (arrows, FIGS. 3L-N), indicative of a heightened formation of autophagic structures in UVA-treated MCEnCs compared to controls. Moreover, levels of autophagy marker LC3-I to -II were increased after 1,000 J/cm$^2$ UVA (FIG. 7F), more so in females than males, and the levels of small mtDNA copy number (measure of mitochondrial content) were mostly constant, except for a small decrease in females at 3 mo. Therefore, UVA did activate auto/mitophagy, as seen in FECD (26-28), demonstrating that lack of ability to remove damaged mitochondria was likely not the cause for the increased mtDNA damage after UVA-induced stress.

UVA Irradiation Elevates CYP1B1 and Promotes Estrogen-DNA Adduct Formation in Female Mice.

Figure 4:
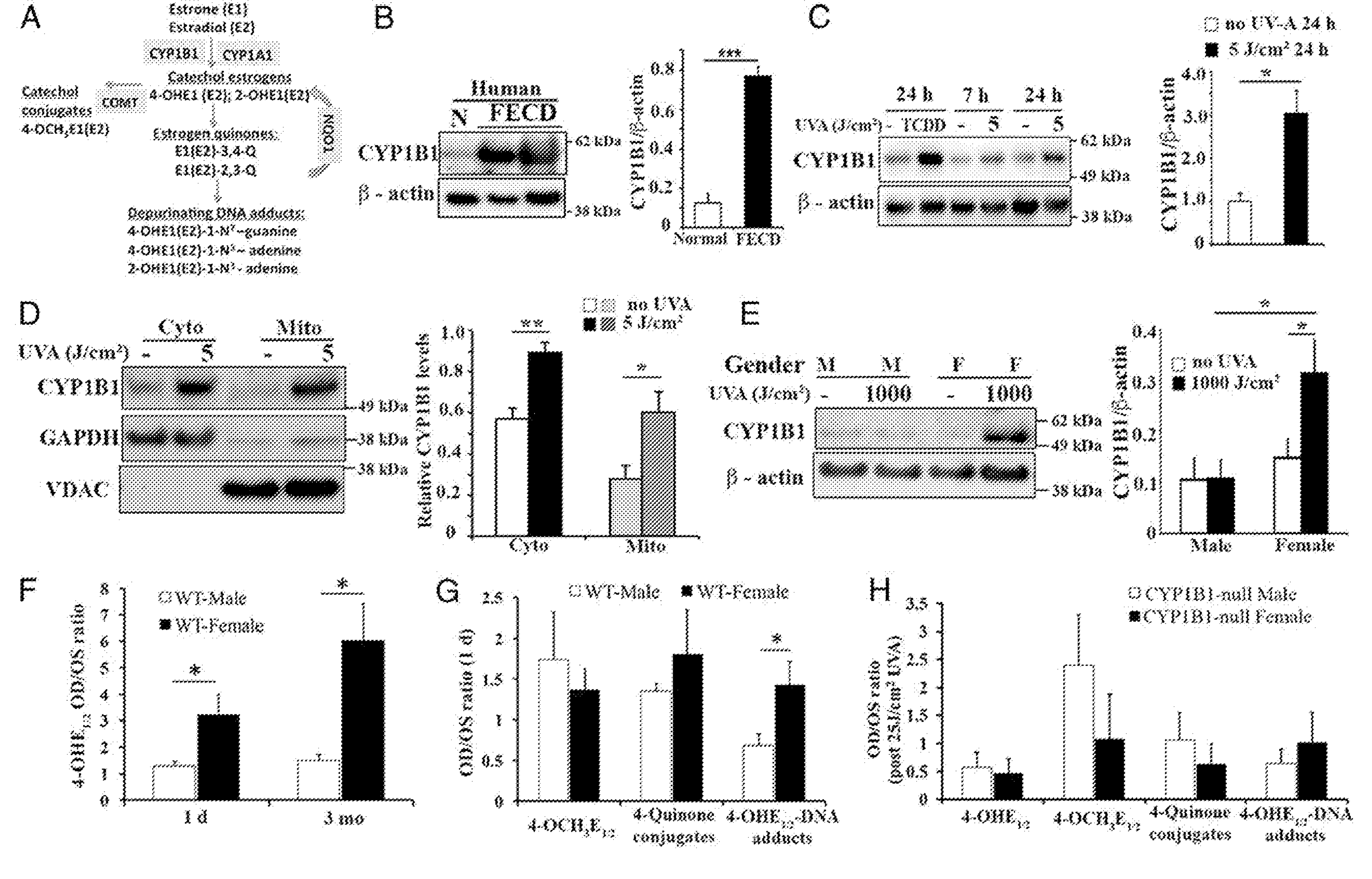
FIGS. 4A-4H. UVA irradiation induced estrogen metabolites in females via enhanced expression levels of CYP1B1.

Based on the findings of a more severe UVA-induced phenotype in female mice, we investigated whether estrogen metabolism is involved in FECD development (FIG. 4A). Specifically, we aimed to explore the role of CYP1B1 and CYP1A1 (Schematic, FIG. 4A), the major estrogen-metabolizing enzymes that trigger the estrogen genotoxic pathway, in accounting for the sex differences in FECD phenotype. Strikingly, we noted significant up-regulation of both CYP1B1 and CYP1A1 protein levels in FECD ex vivo patient specimens compared to donor corneal tissues (FIG. 4B and FIG. 8A). Next, we investigated whether UVA induced CYP1B1 in vitro in CE cells. We treated normal CE cells with 5 J/cm$^2$ UVA and assessed CYP1B1 protein levels at 7 and 24 h postirradiation. CYP1B1 was significantly up-regulated (3-fold) in vitro 24 h after UVA (FIG. 4C). TCDD (2,3,7,8-tetrachlorodibenzo-p-dioxin), an aryl hydrocarbon receptor agonist, served as positive control for CYP1B1 induction (FIG. 4C). In addition to its localization in the endoplasmic reticulum, CYP1B1 is also bimodally targeted to mitochondria via its N-terminal mitochondria localization signal sequences (29). We investigated the subcellular localization of CYP1B1 in normal CE cells upon UVA. CYP1B1 expression increased in the mitochondrial fraction (2.1-fold) along with the cytoplasmic fraction (1.5-fold) 24 h after 5 J/cm$^2$ UVA (FIG. 4D), suggesting possible UVA-mediated mitochondrial translocation of CYP1B1. Furthermore, we assessed CYP1B1 levels in our In vivo UVA model. Interestingly, 1,000 J/cm$^2$ UVA irradiation led to 3-fold upregulation of CYP1B1 in female but not in male mice 1 d post-UVA (FIG. 4E). Similarly, CYP1B1 was up-regulated in female mice with all UVA doses at 3 mo post-UVA, compared to males (FIG. 8B).

Figure 9:
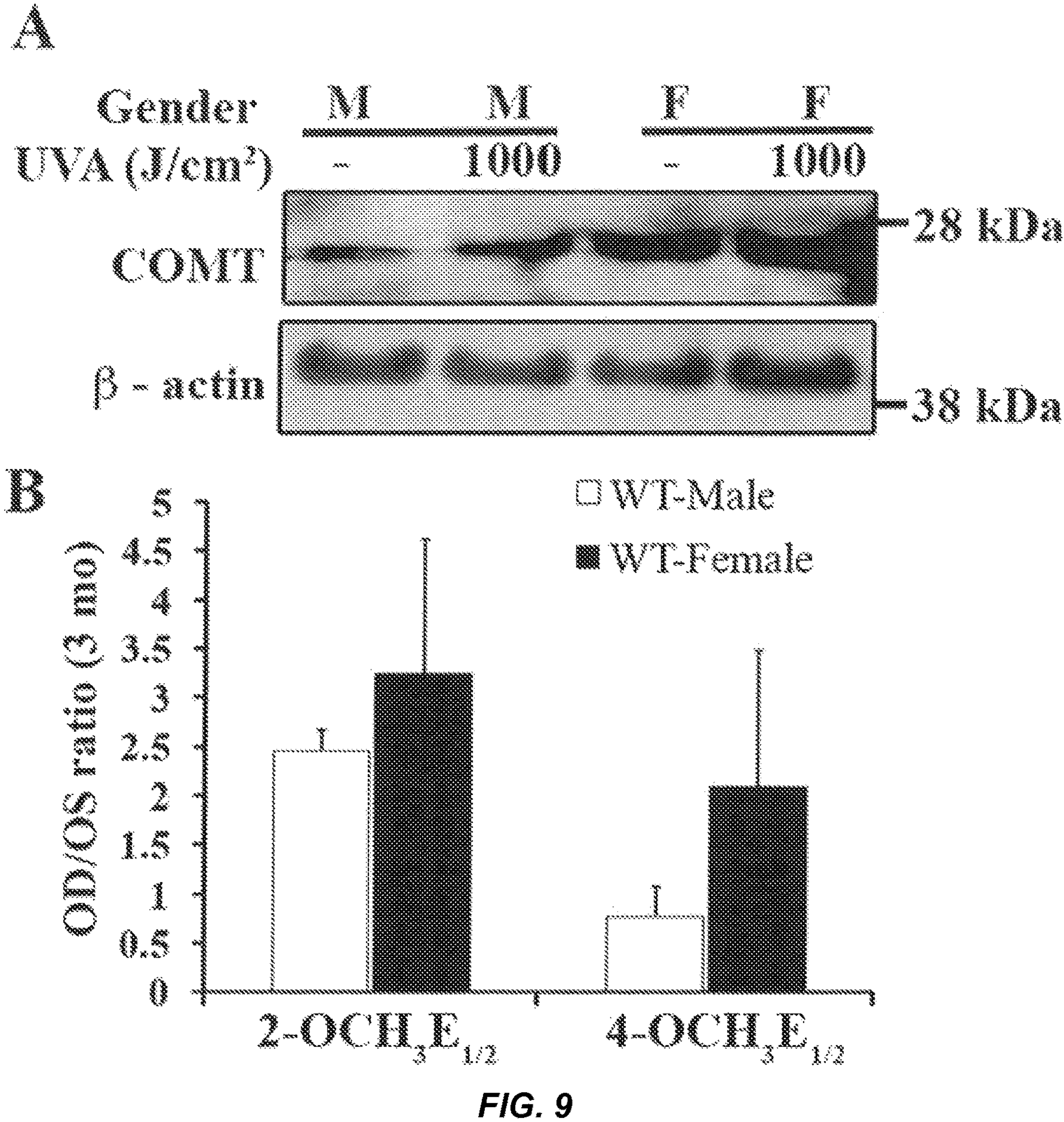
FIGS. 9A-9B.

Since CYP1B1 drives the conversion of $E_{1/2}$ into 4-OHE$_{1/2}$ followed by the generation of catechol estrogen quinones and depurinating DNA adducts (FIG. 4A), we analyzed these estrogen metabolites in the mouse cornea by ultra performance liquid chromatography followed by tandem mass spectrometry (UPLC/MS-MS). To evaluate the changes in levels of estrogen metabolites induced by UVA, we used the ratio of each metabolite from UVA-treated (OD eye) to the nontreated (OS eye) samples. Supporting the increased CYP1B1 expression upon UVA, a significant increase in the ratio of 4-OHE$_{1/2}$ was noted in females at both 1 d and 3 mo post-UVA (FIG. 4F). This accumulated 4-OHE$_{1/2}$ can either be neutralized by the COMT enzyme to methoxy catechol estrogens or be driven toward forming estrogen quinones that later form depurinating DNA adducts (FIG. 4A). COMT levels remained unchanged in both males and females 1 d post-UVA (FIG. 9A). Consistently, 4-methoxy estrogen (4-OCH3E$_{1/2}$) levels also remained unchanged between males and females 1 d postirradiation (FIG. 4G). Therefore, the increased levels of 4-OHE$_{1/2}$-DNA adducts observed in females 1 d postirradiation (FIG. 4G) indicate that the accumulated 4-OHE$_{1/2}$ is driven toward generation of depurinating DNA adducts over its neutralization. We did not detect significant levels of depurinating DNA adducts 3 mo postirradiation, owing to the instability of these adducts being released immediately to the aqueous humor surrounding the endothelial cells and further eliminated from the body. Overall, we speculate that the upregulation of CYP1B1 in ex vivo human FECD specimens could be potentially due to impaired sex hormone pathways in these patients, an underexplored avenue in FECD pathogenesis.

Figure 8:
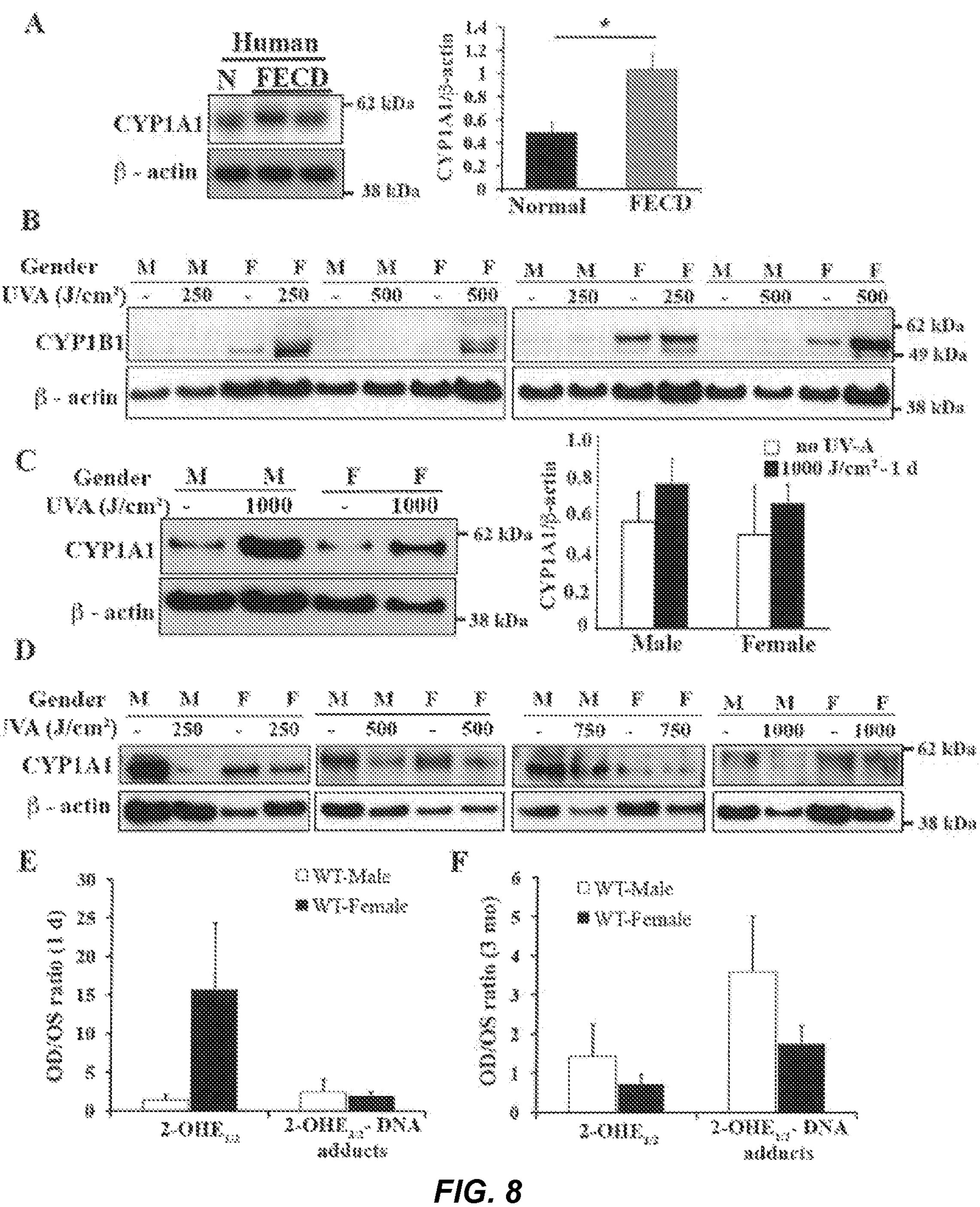
FIGS. 8A-8F.

In contrast to CYP1B1, although CYP1A1 levels were upregulated 1 d post-UV irradiation in vivo, the extent of increase was mostly similar between males and females (FIG. 8C). The ratios of corresponding 2-hydroxyestradiol (2-OHE$_{1/2}$) and 2-OHE$_{1/2}$-DNA adducts were not significantly different between males and females (FIG. 8E) after 1 d of irradiation. Therefore, the increase in 4-OHE$_{1/2}$-DNA adducts seen in females (FIG. 4G) indicates that the majority of estrogen in females is utilized by the increased CYP1B1 driving it to the 4-OHE pathway. Hence, less substrate is available for CYP1A1 to form metabolites in the 2-OHE pathway. This is consistent with the decrease in the 2-OHE$_{1/2}$ ratio (FIG. 8F) with a concomitant increase in the 4-OHE$_{1/2}$ ratio (FIG. 4F) in females compared to males at 3 mo post-UVA. The significance of these observations is strengthened by a previous study which showed that more DNA adducts are formed from 4-OHE$_{1/2}$, thereby forming apurinic sites compared to those formed from 2-$OHE_{1/2}$ (30). Three months after irradiation, CYP1A1 expression did not show significant changes in male and female mice upon UVA (FIG. 8D).

Furthermore, to investigate the importance of differential expression of CYP1B1 in female and male mice, we utilized CYP1B1-null mice for UVA-based studies (31). The cornea of CYP1B1-null mice was treated ex vivo with 25 J/$cm^2$ UVA and harvested for estrogen metabolite analysis as described above. UVA irradiation did not increase the ratio of 4-$OHE_{1/2}$ in either male or female CYP1B1-null mice (FIG. 4H). Similarly, we did not observe any changes in the levels of 4-$OHE_{1/2}$-DNA adducts upon UVA in CYP1B1-null mice (FIG. 4H). Collectively, these data strengthen our hypothesis that differential up-regulation of CYP1B1 in female mice in the UVA model leads to derailed endogenous estrogen metabolism. This causes accumulation of depurinating DNA adducts modeling the DNA damage noted in FECD and provides mechanistic insights on the increased prevalence of FECD in females.

Discussion

FECD is a complex disorder, resulting from the multifactorial interplay of genes and environment. Although multiple genetic associations have been described (32-36), this study points to an important environmental factor involved in FECD development, adding to the body of evidence on the etiology and possible prevention of this common corneal condition. Lack of an In vivo model has impeded the studies on FECD pathophysiology and interventions to inhibit its progression. FECD is a genetically heterogeneous disease associated with mutations of multiple genes and manifests in 2 forms: early-onset and late-onset, the latter being more prevalent (37). Unlike late-onset FECD, which is predominant in females, early-onset FECD occurs equally in both sexes in a 1:1 ratio (38). Missense mutations in the gene encoding the α2 chain of Collagen VIII (COL8A2) have been shown to be associated with the early-onset form of FECD (36, 38), as corroborated by the knock-in mouse model (21, 28). Intronic CTG repeat expansion in the TCF4 gene is the most common genetic marker associated with late-onset FECD that is inherited in an autosomal dominant fashion (39). Apart from TCF4, mutations in KANK4, LAMC1, ATP1B1, SLC4A11, LOXHD1, ZEB1, and AGBL1 have been shown to be associated with FECD (33-35, 40). A recent genome-wide association study identified sex-specific association for LAMC1 and TCF4 in FECD patients (33). Regardless of late-onset FECD genotype, the outcome is susceptibility to oxidative stress (4, 10, 22, 41). The CE is exposed to UV light throughout life and is susceptible to acquired oxidative damage. We based the development of the late-onset and age related form of the FECD model on the physiological outcome of this susceptibility. This study shows that UV light causes FECD, providing evidence of the environmental influences involved in FECD development. Further studies are needed to investigate the interplay between genetic and environmental factors involved in female susceptibility in developing FECD.

We previously showed that UVA activates the Nrf-2-mediated antioxidant pathway and induces apoptosis in corneal endothelial cells in vitro (42). A recent study demonstrated that UVA irradiation (600 J/$cm^2$) of rabbit corneas ex vivo increased redox imbalance in the endothelium compared to the outermost epithelial layer, rendering endothelial cells more susceptible to UVA-induced oxidative damage (6). Safety studies for corneal cross-linking studies done in rabbits have determined that high doses of UVA are cytotoxic to corneal endothelial cells (43, 44). In this study, we simulated the life-long exposure of endothelium to UV light by using high-dose UVA irradiation (1,000 J/$cm^2$) and detected progressive degenerative effects of UVA-mediated damage, modeling FECD in vivo. While exposure to UV is a known factor in other ocular pathologies, including photokeratitis (45, 46), which leads to corneal epithelial damage, in our study, the immediate epithelial defects after irradiation healed within 1 wk. Even though photokeratitis is known to result in endothelial dysfunction (47), these patients do not necessarily develop FECD. The genetic component likely renders the FECD endothelium more susceptible to UVA, and the susceptibility is amplified herein with exposure of mouse corneas to high doses of UVA.

We have detected greater susceptibility of female mice to UVA by showing greater CE cell loss and more prominent morphological changes, as compared to male mice. Moreover, corneal edema was more prominent in female mice, consistent with the epidemiologic studies that have shown other prooxidant factors, such as diabetes and smoking, having a more pronounced effect on the development of corneal edema and FECD progression in female cohorts (15). At the molecular level, female mice showed greater nDNA damage as compared to male mice at a 1-mo time point after UVA, correlating with a lower CE cell number and higher CCT in females. At 3 mo, both female and male mice exhibited nDNA damage, indicating development of a fairly similar "endstage" phenotype in both males and females. However, mtDNA damage, which was induced immediately after UVA irradiation, was repaired at 2 wk and then showed a "secondary" increase only in females at 1 and 3 mo. This reappearance of mtDNA damage only in females likely explains the differential response to UVA between the sexes. Similarly, FECD human specimens exhibited marked reduction in mtDNA amplification, indicating accumulation of basal DNA damage and subsequent mitochondrial dysfunction (10). However, temporal investigation of the animal model provides insight into the possible mechanism at the earlier stages of the disease formation (21) and sheds light on the mechanism of sex differences in FECD that were not explored in previous studies.

Differential susceptibility to UVA between females and males was accompanied by up-regulation of CYP1B1 in female but not male mice at early and late time points after UVA. Previous studies showed up-regulation of CYP1B1 and CYP1A1 in zebrafish (48) and in rats (49) with combined UVA and UVB exposure; however, this study shows that targeted induction of CYP1B1 preferentially in female mice was achieved by In vivo irradiation of the postmitotic ocular tissue with UVA alone, causing CYP1B1-mediated estrogen genotoxicity. Oxidation of tryptophan by UVA irradiation results in the formation of photoproducts that are aryl hydrocarbon receptor (AHR) agonists, thereby inducing CYP1B1 in a human keratinocyte cell line (50). Mutations in CYP1B1 have been reported as the major genetic determinant of primary congenital glaucoma (51). Of interest is the heightened mtDNA damage seen in female mice that is consistent with mitochondrial targeting of CYP1B1 causing oxidative damage to mitochondria (52). The mtDNA is specifically prone to oxidative damage due to lack of protective histones and propagation of ROS-induced lipid peroxidation in the inner mitochondrial membrane (53). Moreover, mtDNA has been shown to be more susceptible to covalent modification by estrogens and formation of estrogen-DNA adducts than nDNA (54, 55), leading to obstruction of mitochondrial gene replication as previously detected in FECD (10, 56). Furthermore, our data showed greater accumulation of depurinating DNA adducts stemming from 4-OHE1(E2) catechol estrogens as compared to 2-OHE1 (E2), consistent with greater activation of CYP1B1. The redox cycling of estrogen quinone derivatives from 4-OHE1 (E2) catechol estrogens has been shown to produce higher levels of depurinating (as opposed to stable) adducts (57), correlating with greater formation of estrogen-driven tumors (17, 18). Higher levels of estrogen DNA adducts are associated with Parkinson's disease and breast cancer, and genetic polymorphisms in CYP1B1 leading to higher adducts are associated with ovarian cancer (58-60). This study provides insights into estrogen metabolism having a physiological relevance in the degenerative loss of postmitotic cells in vivo.

Example 2

Figure 10:
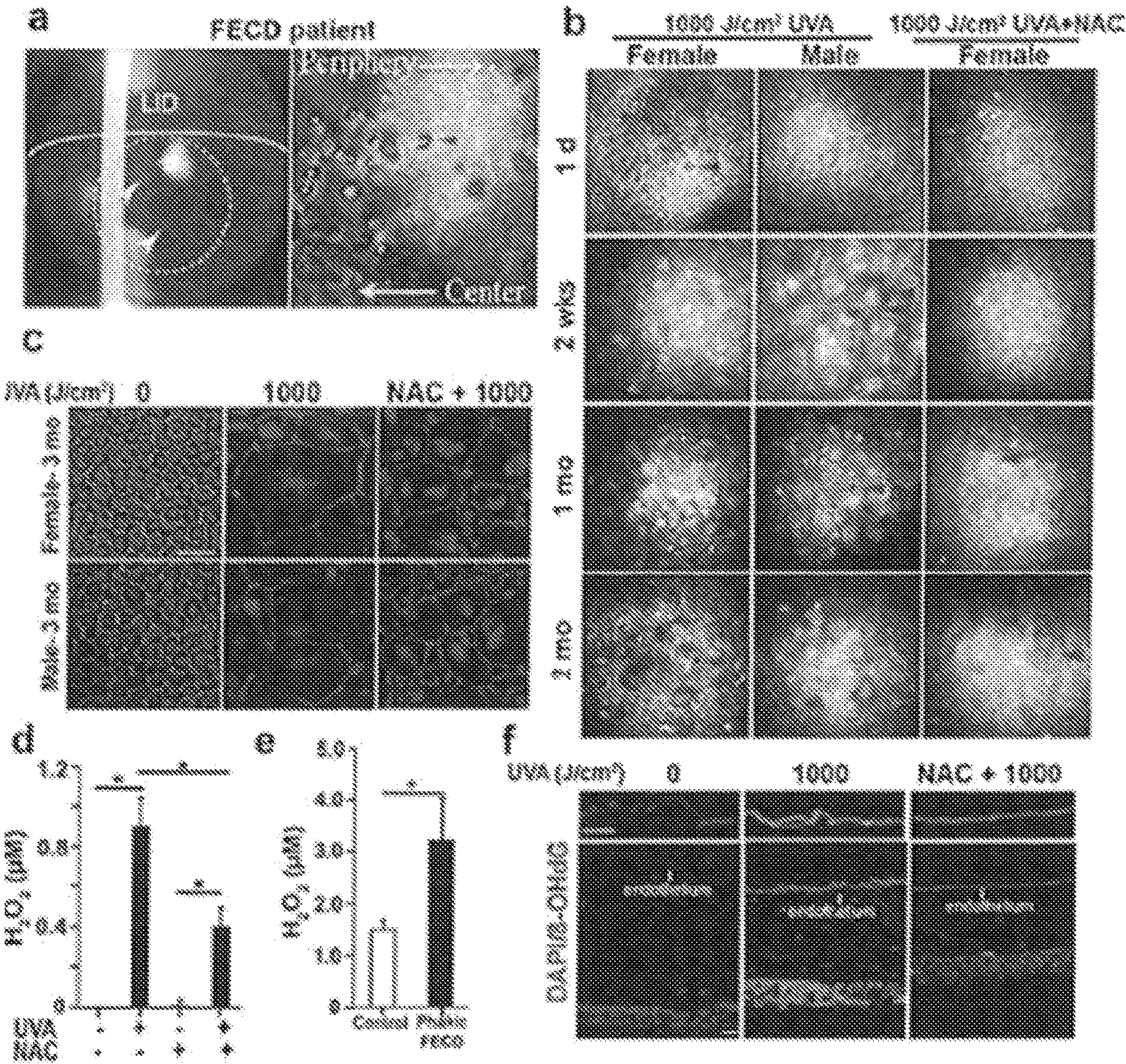
FIGS. 10A-10F. UVA light is a physiological stressor of human eye, known to penetrate the central cornea at a greater level than periphery similarly, cell loss and guttae formation (arrowheads) in FECD patients affects central cornea (FIG. 10A). UVA (1000 J/cm$^2$) induced corneal endothelial cell loss in mouse cornea revealed by In vivo confocal microscopy (Heidelberg Retina Tomograph) (FIG. 10B), morphological changes (cell hypertrophy) as detected by ZO-1 junctional staining (FIG. 10C, increased ROS in mouse aqueous humor resembling the pro-oxidant ocular milieu of FECD patients (FIG. 10D, FIG. 10E) and oxidative DNA damage revealed by 8-OHdG (8-hydroxy-2'-deoxyguanosine) staining on whole-mount corneal sections. The morphological and molecular changes induced by UVA are rescued in vivo by antioxidant N-acetyl cysteine (NAC) (FIGS. 10A-10D, 10F). *P<0.05

The lab developed a novel mouse model of FECD by UVA-irradiation of cornea, leading to the finding that CYP1B1, upregulated by UVA in mouse, catalyzes the formation of 4-hydtoxyestrogen from female estrogen hormone resulting in genotoxic Estrogen-DNA adduct, thus leading to mutation and endothelial cell degeneration (FIG. 10).

Figure 11:
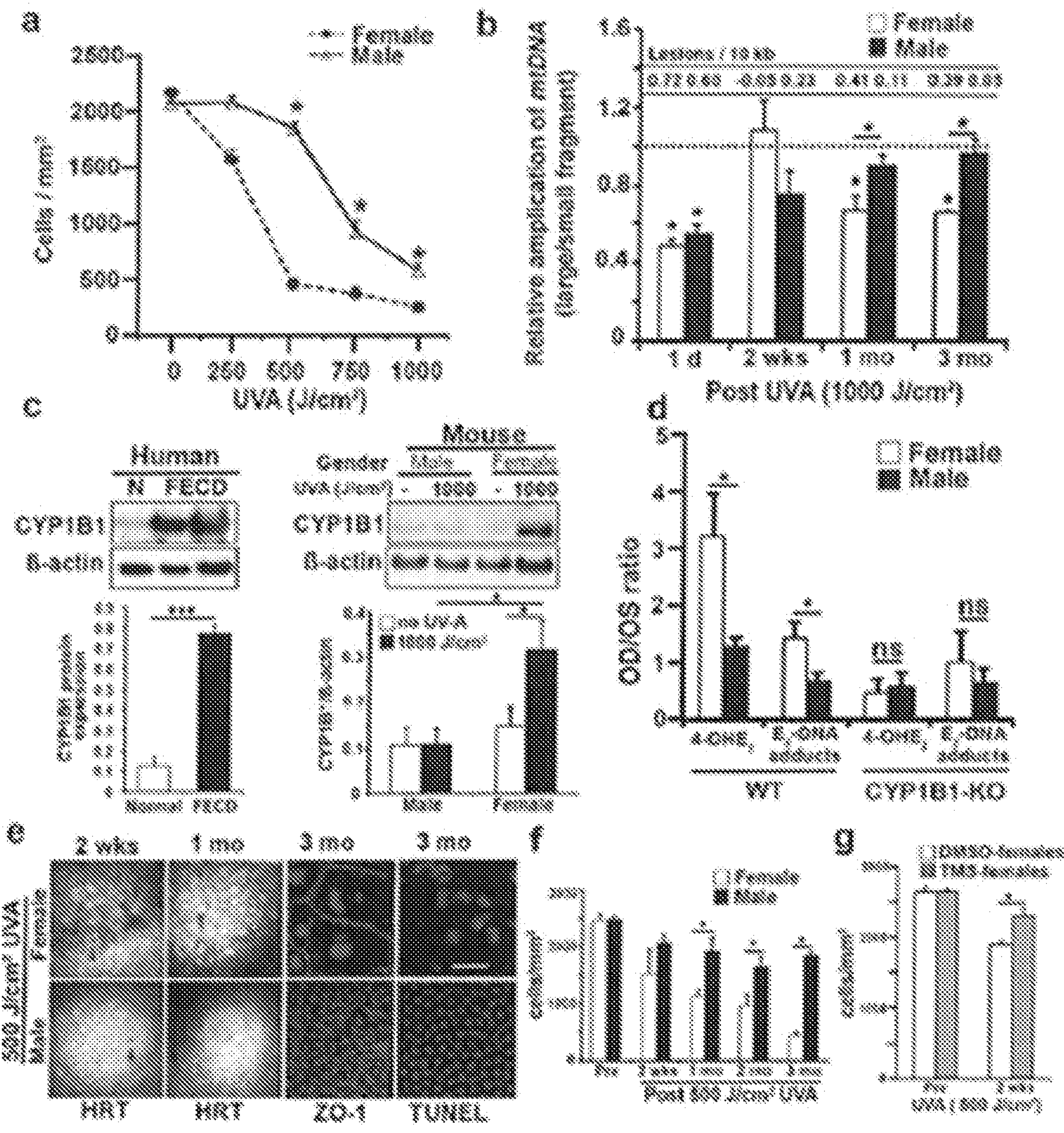
FIGS. 11A-11G. Female mice were more susceptible to UVA-induced endothelial cell loss 3 months post irradiation compared to male mice (FIG. 11A). Females showed greater mitochondrial DNA damage at 1 and 3 months post UVA (1000 J/cm$^2$) irradiation, determined by long-amplicon qPCR analysis (FIG. 11B). Increase in estrogen metabolizing enzyme CYP1B1 in FECD patients was mirrored in female mice post UVA irradiation (FIG. 11C) along with the increase in 4-OHE$_2$ and genotoxic E2-DNA adducts, determined by mass spectrometry. UVA irradiation of CYP1B1-KO corneas ex vivo did not increase 4-OHE$_2$ and E2-DNA adducts in both females and males (FIG. 11D). Increased cell loss, alternation in junctional contacts, and apoptosis in female mice compared to males, determined by in vivo imaging, ZO-1 staining, and TUNEL assay (FIG. 11E, FIG. 11F). Rescue of UVA-induced corneal endothelial cell loss in female mice injected with selective CYP1B1 inhibitor, TMS (trans-2,3',4,5-tetramethoxystilbene) in vivo (FIG. 11G). *P<0.05; *** P<0.001.
Figure 12:
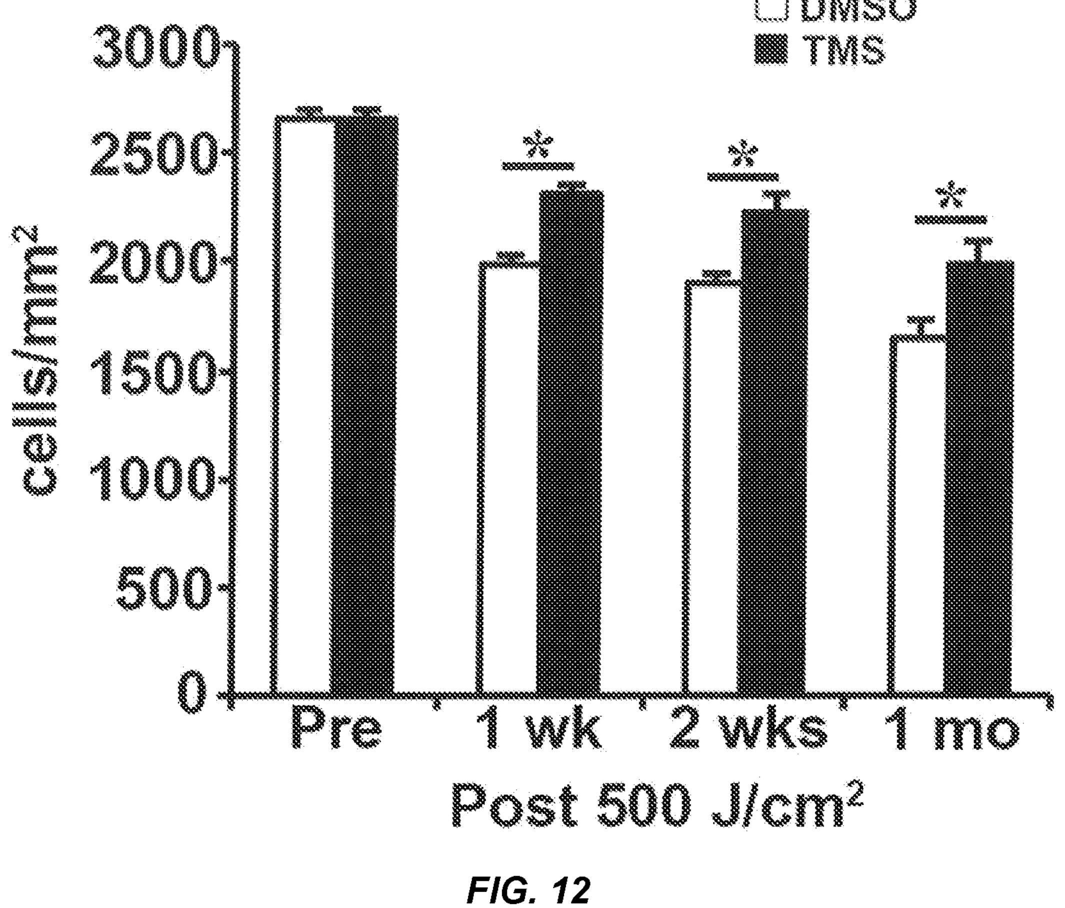
FIG. 12. CYP1B1 inhibitor rescued UVA induced corneal endothelial (CE) cell loss in vivo. Rescue of corneal endothelial cell loss was seen in vivo in female mice at 1 week, 2 weeks and 1 month post 500 J/cm$^2$ irradiation upon treatment with selective CYP1B1 inhibitor TMS (trans-2,3',4,5'-tetramethoxystilbene) (n=6; black bar) *p<0.05 (Student's t test). TMS was injected intraperitoneally (1.5 mg/kg) in female mice 1 h prior to 500 J/cm$^2$ UVA and 3 times a week thereafter for two weeks. Mice similarly injected with DMSO served as the control (n=5; white bar).

The selective CYP1B1 inhibitor TMS (trans-2,3',4,5-tetramethoxystilbene) treatment in mouse model of FECD delayed the endothelial cell degeneration in vivo (FIGS. 11 and 12).

There is no report of pathogenesis regarding female predominance in FECD and no treatment therapy available to prevent or delay the disease progression. CYP1B1 mediated estrogen genotoxicity has been related to other diseases including breast/ovary cancer and Pulmonary Arterial Hypertension. Described herein for the first time is the relationship of CYP1B1 mediated estrogen genotoxicity and female susceptibility to the FECD, which provide new therapeutic avenues for treatment/prevention of female FECD.

Example 3

CYP1B1 inhibitor, TMS (trans-2,3',4,5-tetramethoxystilbene), was evaluated for their ability to rescue UVA light-induced corneal endothelial cell (CEnC) loss in a mouse model of FECD.

Figure 13A:
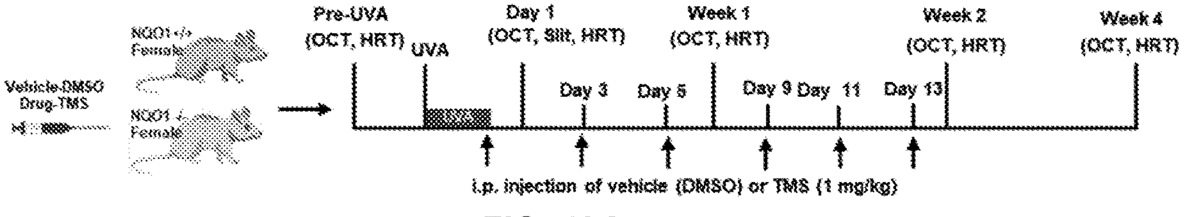
FIGS. 13A-13D. CYP1B1 specific inhibitor (TMS) reduces CEnC loss in the mouse model of Fuchs Dystrophy.

A mouse model of FECD was generated by knocking out the NQO1 gene. NQO1, an important estrogen quinone-detoxifying enzyme regulated by Nrf2 transcription factor, is downregulated in FECD patients, and more importantly, loss of NQO1 generates genotoxic estrogen-DNA adducts in FECD. NQO1+/+ and NQO1−/− female mice were irradiated with UVA (500 J/cm$^2$; time: 20 minutes) to initiate CEnC loss. Either TMS (1 mg/kg) or DMSO (vehicle) was intraperitoneally injected three times a week post-UVA irradiation until week 2 (FIG. 13A). Central corneal thickness (CCT) and Corneal endothelium (CE) imaging was performed using anterior segment-optical coherence tomography (OCT) and Heidelberg Retina Tomograph III (HRT III) prior to UVA irradiation and then at day 1, week 1, week 2, and week 4 post-UVA irradiation. The CE density (cells/mm$^2$) was quantified by a semi-automated cell counter inbuilt in HRT machine.

Figure 13B:
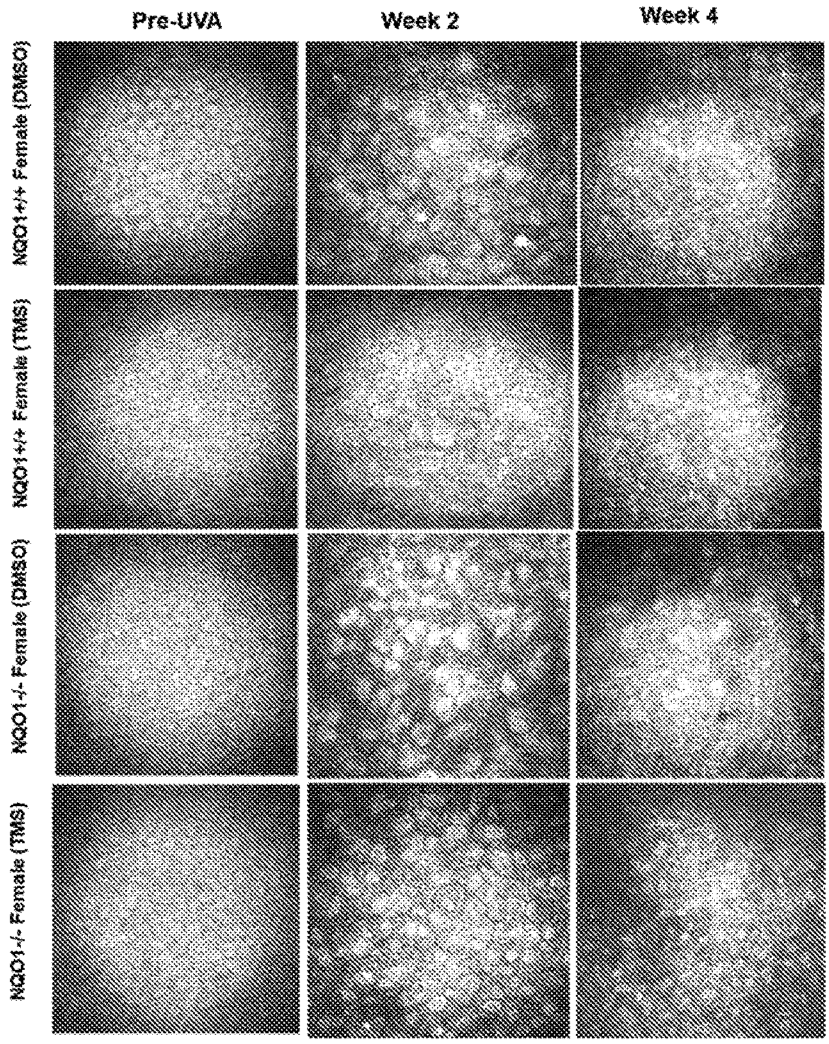
Figure 13C:
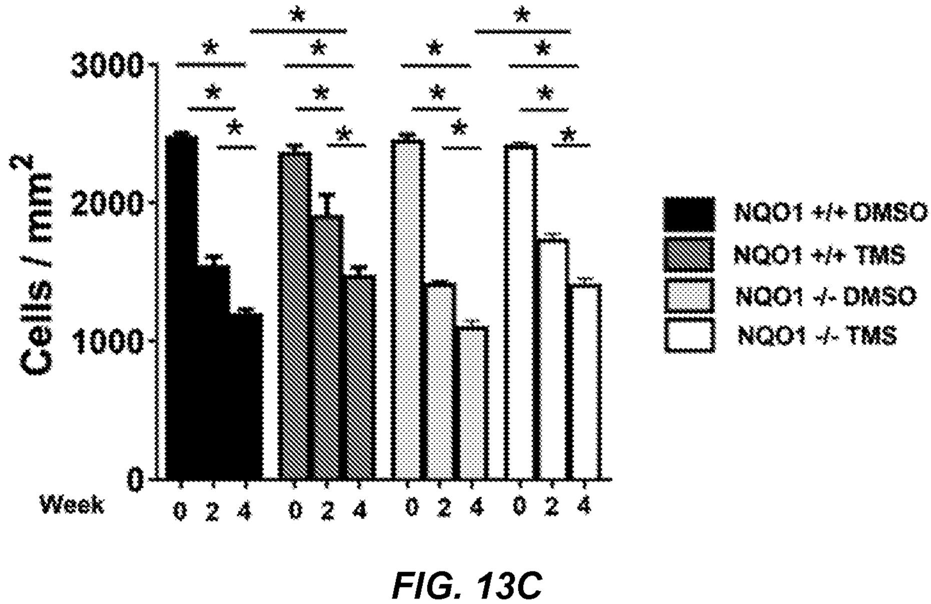
Figure 13D:
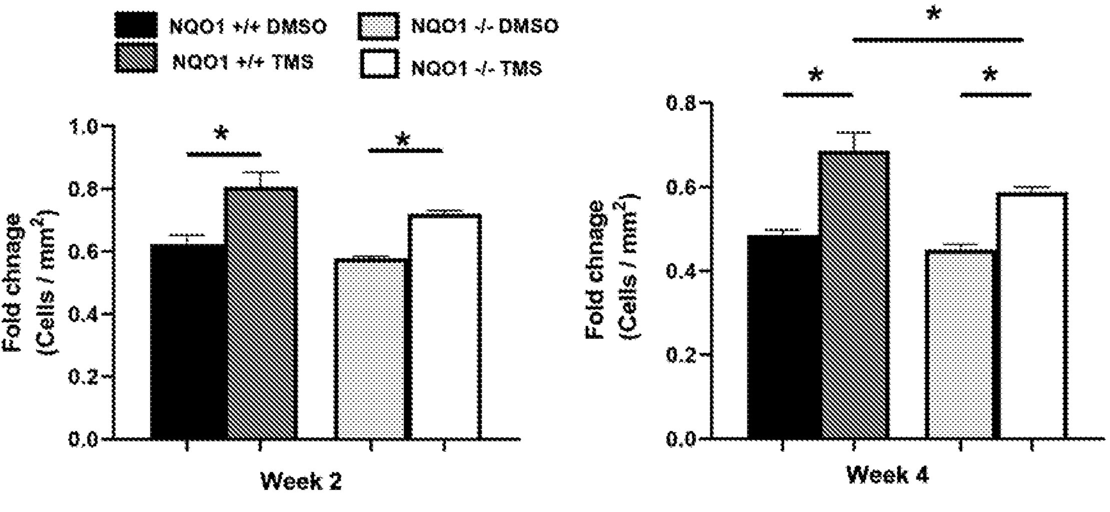

NQO1+/+ and NQO1−/− female mice treated with TMS exhibited less irregular morphology (regular hexagonal shape) of CEnC compared to vehicle treated group at weeks 2 and 4 post-UVA irradiation (FIG. 13B). NQO1+/+ and NQO1−/− female treated with TMS had higher CEnC number compared to vehicle treated mice at weeks 2 and 4 post-UVA (FIGS. 13C, 13D).

Example 4

CYP1B1 inhibitor, berberine, was evaluated for their ability to rescue UVA light-induced corneal endothelial cell (CEnC) loss in a mouse model of FECD.

Figure 14A:
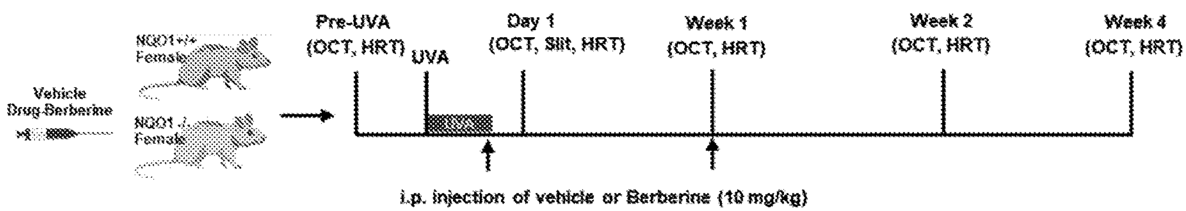
FIGS. 14A-14D. CYP1B1 inhibitor berberine rescues UVA light-induced CEnC loss in the mouse model of Fuchs Dystrophy.

A mouse model of FECD was generated by knocking out the NQO1 gene. NQO1, an important estrogen quinone-detoxifying enzyme regulated by Nrf2 transcription factor, is downregulated in FECD patients, and more importantly, loss of NQO1 generates genotoxic estrogen-DNA adducts in FECD. NQO1+/+ and NQO1−/− female mice were irradiated with UVA (500 J/cm$^2$; time: 20 minutes) to initiate CEnC loss. Either berberine (10 mg/kg) or Vehicle (90% PBS+5% Tween-80+5% polyethylene glycol) was intraperitoneally injected immediately after and at week 1 post-UVA irradiation (FIG. 14A). Central corneal thickness (CCT) and corneal endothelium (CE) imaging was performed using anterior segment-optical coherence tomography (AS-OCT) and Heidelberg Retina Tomograph III (HRT III) prior to UVA irradiation and then at day 1, week 1, and week 2, post-UVA irradiation. The CE density (cells/mm$^2$) was quantified by a semi-automated cell counter inbuilt in HRT machine.

Figure 14B:
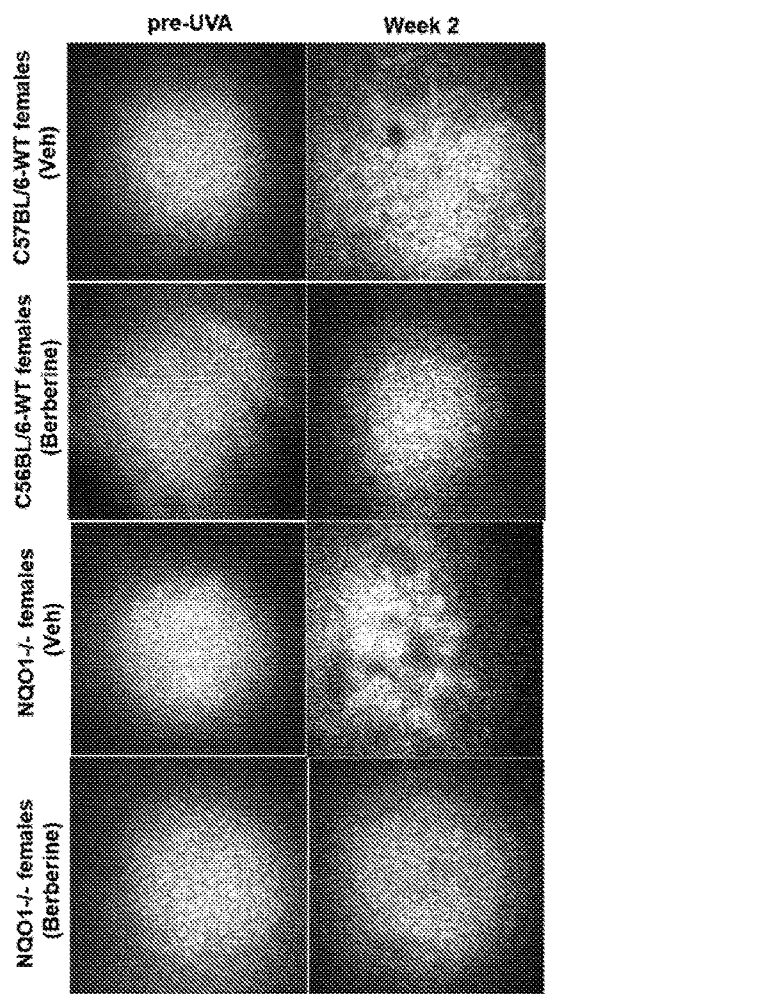
Figure 14C:
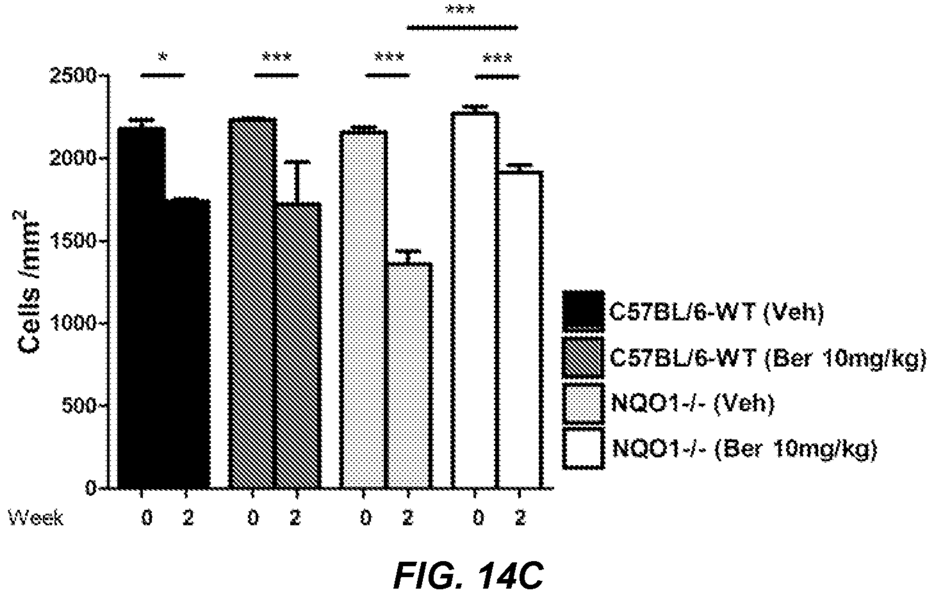
Figure 14D:
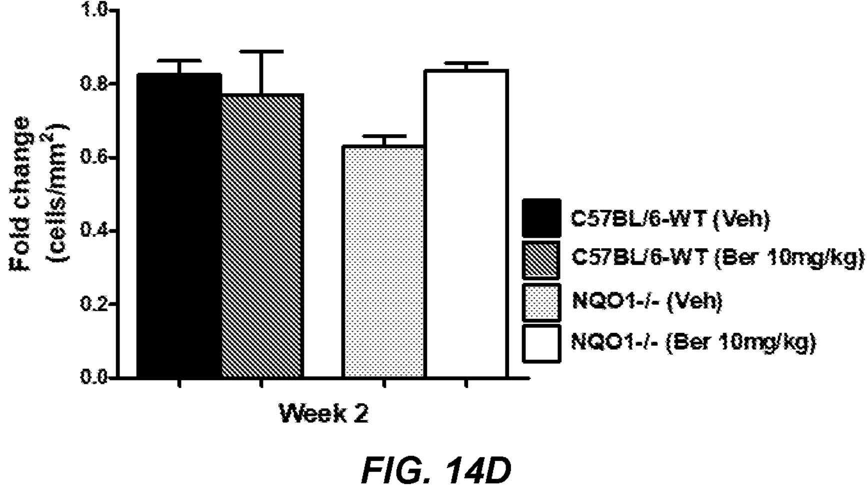

NQO1+/+ and NQO1−/− female mice treated with berberine exhibited less irregular morphology (regular hexagonal shape) of CEnC compared to vehicle treated group at week 2 post-UVA (FIG. 14B). Berberine treatment showed a trend towards higher CEnC number in NQO1+/+ while it showed significantly higher CEnC number indicative of protection in NQO1−/− females compared to vehicle treated mice at week 2 post-UVA (FIGS. 14C, 14D).

REFERENCES

1. N. C. Joyce, Proliferative capacity of the corneal endothelium. Prog. Retin. Eye Res. 22, 359-389 (2003).
2. N. C. Joyce, C. C. Zhu, D. L. Harris, Relationship among oxidative stress, DNA damage, and proliferative capacity in human corneal endothelium. Invest. Ophthalmol. Vis. Sci. 50, 2116-2122 (2009).
3. T. Schmedt, M. M. Silva, A. Ziaei, U. Jurkunas, Molecular bases of corneal endothelial dystrophies. Exp. Eye Res. 95, 24-34 (2012).
4. U. V. Jurkunas, Fuchs endothelial corneal dystrophy through the prism of oxidative stress. Cornea 37 (suppl. 1), S50-S54 (2018).
5. J. J. Doutch, A. J. Quantock, N. C. Joyce, K. M. Meek, Ultraviolet light transmission through the human corneal stroma is reduced in the periphery. Biophys. J. 102, 1258-1264 (2012).
6. C. Zinflou, P. J. Rochette, Ultraviolet A-induced oxidation in cornea: Characterization of the early oxidation-related events. Free Radic. Biol. Med. 108, 118-128 (2017).
7. A. J. Ridley, J. R. Whiteside, T. J. McMillan, S. L. Allinson, Cellular and sub-cellular responses to UVA in relation to carcinogenesis. Int. J. Radiat. Biol. 85, 177-195 (2009).
8. G. F. Vile, R. M. Tyrrell, UVA radiation-induced oxidative damage to lipids and proteins in vitro and in human skin fibroblasts is dependent on iron and singlet oxygen. Free Radic. Biol. Med. 18, 721-730 (1995).

9. N. C. Joyce, D. L. Harris, C. C. Zhu, Age-related gene response of human corneal endothelium to oxidative stress and DNA damage. Invest. Ophthalmol. Vis. Sci. 52, 1641-1649 (2011).

10. A. Halilovic et al., Menadione-induced DNA damage leads to mitochondrial dysfunction and fragmentation during rosette formation in fuchs endothelial corneal dystrophy. Antioxid. Redox Signal. 24, 1072-1083 (2016).

11. P. Yeh, K. Colby, “Corneal endothelial dystrophies” in The Cornea, C. A. D. Foster, C. Dohlman, Eds. (Lippincott Williams & Wilkins, Philadelphia, 2004).

12. S. E. Wilson, W. M. Bourne, Fuchs’ dystrophy. Cornea 7, 2-18 (1988).

13. G. M. Zoega et al., Prevalence and risk factors for cornea guttata in the Reykjavik Eye Study. Ophthalmology 113, 565-569 (2006).

14. M. J. Hogan, I. Wood, M. Fine, Fuchs’ endothelial dystrophy of the cornea. 29th Sanford Gifford Memorial lecture. Am. J. Ophthalmol. 78, 363-383 (1974).

15. X. Zhang et al.; Fuchs’ Genetics Multi-Center Study Group, Association of smoking and other risk factors with Fuchs’ endothelial corneal dystrophy severity and corneal thickness. Invest. Ophthalmol. Vis. Sci. 54, 5829-5835 (2013).

16. A. P. Adamis, V. Filatov, B. J. Tripathi, R. C. Tripathi, Fuchs’ endothelial dystrophy of the cornea. Surv. Ophthalmol. 38, 149-168 (1993).

17. E. Cavalieri et al., Catechol estrogen quinones as initiators of breast and other human cancers: Implications for biomarkers of susceptibility and cancer prevention. Biochim. Biophys. Acta 1766, 63-78 (2006).

18. E. L. Cavalieri, E. G. Rogan, Unbalanced metabolism of endogenous estrogens in the etiology and prevention of human cancer. J. Steroid Biochem. Mol. Biol. 125, 169-180 (2011).

19. J. Hakkola et al., Expression of CYP1B1 in human adult and fetal tissues and differential inducibility of CYP1B1 and CYP1A1 by Ah receptor ligands in human placenta and cultured cells. Carcinogenesis 18, 391-397 (1997).

20. P. Pelkonen, M. Lang, M. Pasanen, Tissue and sex-dependent differences in CYP2A activities in hamsters. Arch. Toxicol. 68, 416-422 (1994).

21. A. S. Jun et al., An alpha 2 collagen VIII transgenic knock-in mouse model of Fuchs endothelial corneal dystrophy shows early endothelial cell unfolded protein response and apoptosis. Hum. Mol. Genet. 21, 384-393 (2012).

22. U. V. Jurkunas, M. S. Bitar, T. Funaki, B. Azizi, Evidence of oxidative stress in the pathogenesis of fuchs endothelial corneal dystrophy. Am. J. Pathol. 177, 2278-2289 (2010).

23. S. Y. Sun, N-acetylcysteine, reactive oxygen species and beyond. Cancer Biol. Ther. 9, 109-110 (2010).

24. J. H. Santos, B. S. Mandavilli, B. Van Houten, Measuring oxidative mtDNA damage and repair using quantitative PCR. Methods Mol. Biol. 197, 159-176 (2002).

25. N. K. Sharma et al., Intrinsic mitochondrial DNA repair defects in Ataxia Telangiectasia. DNA Repair (Amst.) 13, 22-31 (2014).

26. A. S. Benischke et al., Activation of mitophagy leads to decline in Mfn2 and loss of mitochondrial mass in Fuchs endothelial corneal dystrophy. Sci. Rep. 7, 6656 (2017).

27. T. Miyai et al., Activation of PINK1-parkin-mediated mitophagy degrades mitochondrial quality control proteins in fuchs endothelial corneal dystrophy. Am. J. Pathol. 189, 2061-2076 (2019).

28. H. Meng et al., L450W and Q455K Col8a2 knock-in mouse models of Fuchs endothelial corneal dystrophy show distinct phenotypes and evidence for altered autophagy. Invest. Ophthalmol. Vis. Sci. 54, 1887-1897 (2013).

29. M. C. Sangar, S. Bansal, N. G. Avadhani, Bimodal targeting of microsomal cytochrome P450s to mitochondria: Implications in drug metabolism and toxicity. Expert Opin. Drug Metab. Toxicol. 6, 1231-1251 (2010).

30. E. L. Cavalieri, E. G. Rogan, M. Zahid, Critical depurinating DNA adducts: Estrogen adducts in the etiology and prevention of cancer and dopamine adducts in the etiology and prevention of Parkinson’s disease. Int. J. Cancer 141, 1078-1090 (2017).

31. J. T. Buters et al., Cytochrome P450 CYP1B1 determines susceptibility to 7, 12-dimethylbenz[a]anthracene-induced lymphomas. Proc. Natl. Acad. Sci. U.S.A. 96, 1977-1982 (1999).

32. K. H. Baratz et al., E2-2 protein and Fuchs’s corneal dystrophy. N. Engl. J. Med. 363, 1016-1024 (2010).

33. N. A. Afshari et al., Genome-wide association study identifies three novel loci in Fuchs endothelial corneal dystrophy. Nat. Commun. 8, 14898 (2017).

34. S. A. Riazuddin et al., Mutations in LOXHD1, a recessive-deafness locus, cause dominant late-onset Fuchs corneal dystrophy. Am. J. Hum. Genet. 90, 533-539 (2012).

35. D. W. Chung, R. F. Frausto, L. B. Ann, M. S. Jang, A. J. Aldave, Functional impact of ZEB1 mutations associated with posterior polymorphous and Fuchs’ endothelial corneal dystrophies. Invest. Ophthalmol. Vis. Sci. 55, 6159-6166 (2014).

36. S. Biswas et al., Missense mutations in COL8A2, the gene encoding the alpha2 chain of type VIII collagen, cause two forms of corneal endothelial dystrophy. Hum. Mol. Genet. 10, 2415-2423 (2001).

37. M. Matthaei et al., Fuchs endothelial corneal dystrophy: Clinical, genetic, pathophysiologic, and therapeutic aspects. Annu. Rev. Vis. Sci. 5, 151-175 (2019).

38. J. D. Gottsch et al., Inheritance of a novel COL8A2 mutation defines a distinct earlyonset subtype of fuchs corneal dystrophy. Invest. Ophthalmol. Vis. Sci. 46, 1934-1939 (2005).

39. E. D. Wieben et al., A common trinucleotide repeat expansion within the transcription factor 4 (TCF4, E2-2) gene predicts Fuchs corneal dystrophy. PLoS One 7, e49083 (2012).

40. J. Zhang, C. N. J. McGhee, D. V. Patel, The molecular basis of fuchs’ endothelial corneal dystrophy. Mol. Diagn. Ther. 23, 97-112 (2019).

41. U. V. Jurkunas et al., Decreased expression of peroxiredoxins in Fuchs’ endothelial dystrophy. Invest. Ophthalmol. Vis. Sci. 49, 2956-2963 (2008).

42. C. Liu, D. Vojnovic, I. E. Kochevar, U. V. Jurkunas, UV-A irradiation activates Nrf2-regulated antioxidant defense and induces p53/caspase3-dependent apoptosis in corneal endothelial cells. Invest. Ophthalmol. Vis. Sci. 57, 2319-2327 (2016).

43. G. Wollensak, E. Spoerl, M. Wilsch, T. Seiler, Endothelial cell damage after riboflavinultraviolet-A treatment in the rabbit. J. Cataract Refract. Surg. 29, 1786-1790 (2003).

44. G. Wollensak, E. Sporl, F. Reber, L. Pillunat, R. Funk, Corneal endothelial cytotoxicity of riboflavin/UVA treatment in vitro. Ophthalmic Res. 35, 324-328 (2003).

45. A. P. Cullen, Photokeratitis and other phototoxic effects on the cornea and conjunctiva. Int. J. Toxicol. 21, 455-464 (2002).
46. A. R. Young, Acute effects of UVR on human eyes and skin. Prog. Biophys. Mol. Biol. 92, 80-85 (2006).
47. J. P. Bergmanson, Corneal damage in photokeratitis—Why is it so painful? Optom. Vis. Sci. 67, 407-413 (1990).
48. L. Behrendt, M. E. Jonsson, J. V. Goldstone, J. J. Stegeman, Induction of cytochrome P450 1 genes and stress response genes in developing zebrafish exposed to ultraviolet radiation. Aquat. Toxicol. 98, 74-82 (2010).
49. G. Goerz et al., Influence of UVA and UVB irradiation on hepatic and cutaneous P450 isoenzymes. Arch. Dermatol. Res. 289, 46-51 (1996).
50. R. K. Sindhu, F. E. Wagner, Y. Kikkawa, Induction of cytochrome p450 1A1 and 1B1 by photooxidized tryptophan in transformed human keratinocytes. Adv. Exp. Med. Biol. 527, 297-306 (2003).
51. V. Vasiliou, F. J. Gonzalez, Role of CYP1B1 in glaucoma. Annu. Rev. Pharmacol. Toxicol. 48, 333-358 (2008).
52. S. Bansal et al., Mitochondrial targeting of cytochrome P450 (CYP) 1B1 and its role in polycyclic aromatic hydrocarbon-induced mitochondrial dysfunction. J. Biol. Chem. 289, 9936-9951 (2014).
53. F. M. Yakes, B. Van Houten, Mitochondrial DNA damage is more extensive and persists longer than nuclear DNA damage in human cells following oxidative stress. Proc. Natl. Acad. Sci. U.S.A. 94, 514-519 (1997).
54. R. D. Thomas, D. Roy, Stilbene estrogen produces higher levels of mitochondrial DNA adducts than nuclear DNA adducts in the target organ of cancer (liver) of male Sprague Dawley rats. Oncol. Rep. 8, 1035-1038 (2001).
55. R. D. Thomas, D. Roy, Base sequence-specific attack of stilbene estrogen metabolite(s) on the mitochondrial DNA: Implications in the induction of instability in the mitochondrial genome in the kidney of Syrian hamsters. Int. J. Mol. Med. 7, 389-395 (2001).
56. J. D. Gottsch et al., Serial analysis of gene expression in the corneal endothelium of Fuchs' dystrophy. Invest. Ophthalmol. Vis. Sci. 44, 594-599 (2003).
57. E. L. Cavalieri et al., Molecular origin of cancer: Catechol estrogen-3,4-quinones as endogenous tumor initiators. Proc. Natl. Acad. Sci. U.S.A. 94, 10937-10942 (1997).
58. N. W. Gaikwad et al., Imbalanced estrogen metabolism in the brain: Possible relevance to the etiology of Parkinson's disease. Biomarkers 16, 434-444 (2011).
59. S. Pruthi et al., Evaluation of serum estrogen-DNA adducts as potential biomarkers for breast cancer risk. J. Steroid Biochem. Mol. Biol. 132, 73-79 (2012).
60. M. Zahid et al., Unbalanced estrogen metabolism in ovarian cancer. Int. J. Cancer 134, 2414-2423 (2014).
61. S. L. Byers, M. V. Wiles, S. L. Dunn, R. A. Taft, Mouse estrous cycle identification tool and images. PLoS One 7, e35538 (2012).
62. T. Schmedt et al., Telomerase immortalization of human corneal endothelial cells yields functional hexagonal monolayers. PLoS One 7, e51427 (2012).
63. B. Mondal et al., Modulation of cellular response to arsenic trioxide toxicity by resveratrol. ACS Omega 3, 5511-5515 (2018).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting or treating Fuchs endothelial corneal dystrophy (FECD) in a subject, the method comprising administering to the subject a therapeutically effective dose of a cytochrome P450 enzyme inhibitor, wherein the cytochrome P450 enzyme inhibitor is trans-2, 3', 4, 5'-tetramethoxystilbene.

2. The method of claim 1, wherein the subject has had previous cataract surgery.

3. The method of claim 1, wherein administration is made locally to the eye.

4. The method of claim 3, wherein local administration to the eye is by topical administration or by eye drops.

5. The method of claim 1, wherein the subject is human.

6. The method of claim 5, wherein the subject is female.

* * * * *